(12) United States Patent
Klug et al.

(10) Patent No.: US 9,622,959 B2
(45) Date of Patent: Apr. 18, 2017

(54) CROSS-LINKED POLYMERE

(75) Inventors: Peter Klug, Grossostheim (DE); Dirk Fischer, Klein-Winternheim (DE); Thomas Lindner, Wiesbaden (DE); Wiebke Mueckenheim, Bad Soden (DE); Bianca Brasch, Aura im Sinngrund (DE); Michael Hornung, Frankfurt am Main (DE)

(73) Assignee: CLARIANT INTERNATIONAL LTD., Muttenz (CH)

( * ) Notice: Subject to any disclaimer, the term of this patent is extended or adjusted under 35 U.S.C. 154(b) by 0 days.

(21) Appl. No.: 14/003,340

(22) PCT Filed: Mar. 3, 2012

(86) PCT No.: PCT/EP2012/000969
§ 371 (c)(1),
(2), (4) Date: Dec. 11, 2013

(87) PCT Pub. No.: WO2012/119747
PCT Pub. Date: Sep. 13, 2012

(65) Prior Publication Data
US 2014/0127147 A1    May 8, 2014

(30) Foreign Application Priority Data

Mar. 8, 2011 (DE) .................. 10 2011 013 342

(51) Int. Cl.
| | | |
|---|---|---|
| *A61K 8/81* | (2006.01) |
| *A61K 47/32* | (2006.01) |
| *A61Q 5/06* | (2006.01) |
| *A61Q 5/08* | (2006.01) |
| *A61Q 5/02* | (2006.01) |
| *A61Q 15/00* | (2006.01) |
| *A61Q 19/02* | (2006.01) |
| *A61Q 19/08* | (2006.01) |
| *A61Q 17/04* | (2006.01) |
| *A61Q 19/00* | (2006.01) |
| *C08F 220/58* | (2006.01) |
| *A61K 31/02* | (2006.01) |
| *A61K 31/19* | (2006.01) |
| *A61K 31/192* | (2006.01) |
| *A61K 31/375* | (2006.01) |
| *A61K 31/60* | (2006.01) |
| *A61K 31/795* | (2006.01) |
| *A61K 45/06* | (2006.01) |
| *A61Q 1/14* | (2006.01) |
| *A61Q 5/04* | (2006.01) |
| *A61Q 5/10* | (2006.01) |
| *A61Q 17/00* | (2006.01) |
| *A61Q 19/04* | (2006.01) |
| *A61Q 19/10* | (2006.01) |

(Continued)

(52) U.S. Cl.
CPC ............ *A61K 8/8158* (2013.01); *A61K 31/02* (2013.01); *A61K 31/19* (2013.01); *A61K 31/192* (2013.01); *A61K 31/375* (2013.01); *A61K 31/60* (2013.01); *A61K 31/795* (2013.01); *A61K 45/06* (2013.01); *A61K 47/32* (2013.01); *A61Q 1/02* (2013.01); *A61Q 1/14* (2013.01); *A61Q 5/02* (2013.01); *A61Q 5/04* (2013.01); *A61Q 5/06* (2013.01); *A61Q 5/065* (2013.01); *A61Q 5/08* (2013.01); *A61Q 5/10* (2013.01); *A61Q 15/00* (2013.01); *A61Q 17/005* (2013.01); *A61Q 17/04* (2013.01); *A61Q 19/00* (2013.01); *A61Q 19/02* (2013.01); *A61Q 19/04* (2013.01); *A61Q 19/08* (2013.01); *A61Q 19/10* (2013.01); *C08F 220/56* (2013.01); *C08F 220/58* (2013.01); *C09J 4/00* (2013.01); *A61K 2800/48* (2013.01)

(58) Field of Classification Search
None
See application file for complete search history.

(56) References Cited

U.S. PATENT DOCUMENTS

| 5,185,395 A | 2/1993 | Robinson et al. |
| 5,879,718 A | 3/1999 | Sebillote-Arnaud |

(Continued)

FOREIGN PATENT DOCUMENTS

| CA | 2 209 060 | 12/1997 |
| DE | 10 2009 01487 | 9/2009 |

(Continued)

OTHER PUBLICATIONS

International Search Report for PCT/EP2010/001755, dated May 21, 2010.

(Continued)

*Primary Examiner* — Jianfeng Song
(74) *Attorney, Agent, or Firm* — Tod A. Waldrop

(57) ABSTRACT

The invention relates to water-soluble or water-swellable polymers the repeating structural units of which consist of a) 90.0 to 99.99 mole-% of one or more repeating structural units originating from special monomers with sulfonic acid groups or the salts thereof such as for example 2-acry-lamido-2-methyl-propanesulfonic acid or the salts thereof and b) 0.01 to 10.0 mole-% of one or more repeating structural units originating from special cross-linking agents with at least three polymerizable double bonds. The polymers for example have an advantageous sensory property profile and are highly suitable as thickening agents even in salt-containing compositions. They are furthermore advantageously suitable for producing cosmetic, dermatological or pharmaceutical compositions.

17 Claims, No Drawings

(51) Int. Cl.
*C08F 220/56* (2006.01)
*C09J 4/00* (2006.01)
*A61Q 1/02* (2006.01)

(56) References Cited

U.S. PATENT DOCUMENTS

| | | | |
|---|---|---|---|
| 5,891,452 A | 4/1999 | Sebillote-Arnaud et al. | |
| 5,952,395 A | 9/1999 | Lorant | |
| 6,120,780 A * | 9/2000 | Dupuis et al. | 424/401 |
| 6,180,118 B1 | 1/2001 | Maubru | |
| 6,437,068 B2 | 8/2002 | Loeffler et al. | |
| 6,468,549 B1 | 10/2002 | Dupuis et al. | |
| 6,509,024 B2 | 1/2003 | Lorant | |
| 6,596,264 B2 | 7/2003 | Terren et al. | |
| 2003/0108497 A1 | 6/2003 | Chevalier et al. | |
| 2007/0166269 A1 | 7/2007 | Cassin et al. | |
| 2008/0014154 A1 | 1/2008 | Mougin et al. | |
| 2011/0110878 A1 | 5/2011 | Knappe et al. | |
| 2011/0224361 A1* | 9/2011 | Daniel | C08F 220/06 524/556 |
| 2012/0100084 A1* | 4/2012 | Peter et al. | 424/59 |
| 2014/0086854 A1 | 3/2014 | Klug et al. | |

FOREIGN PATENT DOCUMENTS

| | | | |
|---|---|---|---|
| DE | 102009014877 | * | 9/2009 |
| EP | 0 036 294 | | 10/1981 |
| EP | 0 574 202 | | 12/1993 |
| EP | 0 699 726 | | 3/1996 |
| EP | 0 816 403 | | 1/1997 |
| EP | 0 815 828 | | 1/1998 |
| EP | 0 815 843 | | 1/1998 |
| EP | 0 815 844 | | 1/1998 |
| EP | 0 815 845 | | 1/1998 |
| EP | 0 815 846 | | 1/1998 |
| EP | 0 815 847 | | 1/1998 |
| EP | 0 829 258 | | 3/1998 |
| EP | 1 116 733 | | 7/2001 |
| EP | 1 136 058 | | 9/2001 |
| EP | 1 325 729 | | 9/2003 |
| EP | 1447074 | * | 8/2004 |
| EP | 1 468 670 | | 10/2004 |
| EP | 1 746 114 | | 1/2007 |
| FR | 2 910 899 | | 7/2008 |
| WO | WO 90/12822 | | 11/1990 |
| WO | WO 2010/009953 | | 1/2010 |

OTHER PUBLICATIONS

Translation of the International Preliminary Report on Patentability for PCT/EP2010/001755, dated Sep. 27, 2011.
Translation of the Written Opinion of the International Searching Authority for PCT/EP2010/001755, dated Sep. 27, 2011.
Safety Data Sheet for "BETA-C", Bimax Chemicals Ltd., London, United Kingdom, Mar. 8, 2011.
English Abstract for EP 0 699 726, Mar. 6, 1996.
English Abstract for EP 1 325 729, Sep. 7, 2003.
English Abstract for EP 1 468 670, Oct. 20, 2004.
English Abstract for FR 2 910 899, Jul. 4, 2008.
International Search Report for PCT/EP2012/000969, dated Aug. 20, 2012.
International Search Report for PCT/EP2012/000968, dated Aug. 20, 2012.

* cited by examiner

CROSS-LINKED POLYMERE

The present invention relates to polymers with structural units derived from special monomers with sulfonic acid groups or the corresponding sulfonates, e.g. 2-acrylamido-2-methyl-propanesulfonic acid or salts thereof and with structural units derived from special trifunctional crosslinking agents, a method of producing said polymers, cosmetic, dermatological or pharmaceutical compositions containing one or more of said polymers and particular uses of said polymers, e.g. the use of said polymers as sensory additive, thickener or consistency agent.

Polymers based on 2-acrylamido-2-methyl-propanesulfonic acid or salts thereof are already known.

For example, EP 0 816 403 (Clariant) describes water-soluble or water-swellable polymers based on 2-acrylamido-2-methyl-propanesulfonates. The following are mentioned as crosslinking monomers: dipropylene glycol diallyl ether, polyglycol diallyl ether, triethylene glycol divinyl ether, hydroquinone diallyl ether, tetraallyloxyethane, tetraethylene glycol diacrylate, triallylamine, trimethylolpropane diallyl ether, methylene bisacrylamide, divinylbenzene, trimethylolpropane triacrylate (TMPTA) and trimethylolpropane trimethacrylate (TMPTMA).

These polymers swell in water over a wide range of pH and are easy to handle. They have been used extensively in the cosmetics industry, as described for example in EP 0 815 843, EP 0 815 844, EP 0 815 845, EP 0 815 846, EP 0 815 847, EP 0 815 828, EP 0 829 258, EP 1 136 058, EP 1 325 729 and EP 1 468 670 (L'Oréal).

However, it is not possible, with the aforementioned crosslinked polymers, to cover all sensory property profiles in cosmetic, dermatological or pharmaceutical compositions and moreover their salt stability is often in need of improvement.

The problem to be solved by the present invention was therefore to provide polymers which, especially in cosmetic, dermatological and pharmaceutical compositions, supply a sensorily optimized property profile, e.g. a rich, caring skin feel and moreover are suitable advantageously as thickener also in salt-containing compositions such as in water-containing salt-containing compositions.

It was found, surprisingly, that this problem is solved with polymers based on special monomers with sulfonic acid groups or salts thereof of the following formula (1), e.g. 2-acrylamido-2-methyl-propanesulfonic acid or sulfonates and special trifunctional crosslinking agents of the following formula (2).

The invention therefore relates to water-soluble or water-swellable polymers, the repeating structural units of which consist of a) 90.0 to 99.99 mol %, preferably 92.0 to 99.9 mol %, especially preferably 97.0 to 99.75 mol % and quite especially preferably 98.0 to 99.5 mol % of one or more repeating structural units that are independent of one another, of formula (1)

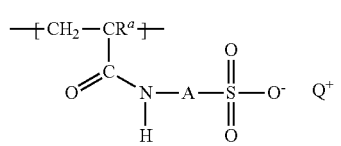

in which
$R^a$ denotes hydrogen, methyl or ethyl,
A denotes linear or branched $C_1$-$C_{12}$ alkylene, preferably $C_1$-$C_8$ alkylene, and
$Q^+$ stands for $H^+$, $NH_4^+$, organic ammonium ions $[HNR^5R^6R^7]^+$, wherein $R^5$, $R^6$ and $R^7$ can be, independently of one another, hydrogen, a linear or branched alkyl group with 1 to 22 carbon atoms, a linear or branched, singly or multiply unsaturated alkenyl group with 2 to 22 carbon atoms, a $C_6$-$C_{22}$ alkylamidopropyl group, a linear monohydroxyalkyl group with 2 to 10 carbon atoms or a linear or branched dihydroxyalkyl group with 3 to 10 carbon atoms, and wherein at least one of the residues $R^5$, $R^6$ and $R^7$ is not hydrogen, alkali$^+$, wherein alkali$^+$ is preferably Li$^+$, Na$^+$ and K$^+$, ½ alkaline earth$^{++}$, wherein ½ alkaline earth$^{++}$ is preferably ½ Ca$^{++}$ and ½ Mg$^{++}$, ½ Zn$^{++}$ or ⅓ Al$^{+++}$ or for mixtures of these ions, and
b) 0.01 to 10.0 mol %, preferably 0.1 to 8.0 mol %, especially preferably 0.25 to 3.0 mol % and quite especially preferably 0.5 to 2.0 mol % of one or more repeating crosslinking structural units that are independent of one another, of formula (2)

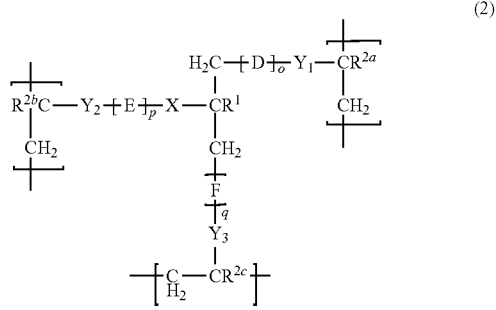

in which
$R^1$ denotes hydrogen, methyl, ethyl, methylol (—$CH_2$—OH) or ethylol (—$CH_2$—$CH_2$—OH),
$R^{2a}$, $R^{2b}$ and $R^{2c}$ in each case independently of one another, denote hydrogen, methyl or ethyl,
X denotes a chemical bond, methylene (—$CH_2$—), ethylene (—$CH_2$—$CH_2$—) or a linear or branched alkylene group with 3 carbon atoms,
$Y_1$, $Y_2$ and $Y_3$ in each case independently of one another, denote a chemical bond, O, $CH_2$, C(O)O, OC(O), C(O)NR$^3$ or NR$^3$C(O),
$R^3$ denotes hydrogen or a linear or branched alkyl residue with 1 to 50 carbon atoms,
D, E and F in each case independently of one another, denote methylene-oxy, ethylene-oxy, propylene-oxy, a linear or branched alkylene group with 1 to 6 carbon atoms, a linear or branched, singly or multiply unsaturated alkenylene group with 2 to 6 carbon atoms, a linear or branched monohydroxyalkylene group with 2 to 6 carbon atoms or a linear or branched dihydroxyalkylene group with 3 to 6 carbon atoms, and
o, p and q in each case independently of one another, denote integers from 0 to 50 and the sum o+p+q≥3.

For production of the polymers according to the invention, only the monomers from which ultimately the one or more repeating structural units of formula (1) are derived, and additionally only the monomers from which the one or more repeating structural units of formula (2) are derived, are polymerized as polymerizable monomers. No other polymerizable monomers additional to these monomers are used for producing the polymers according to the invention.

The molar amounts (in mol %) stated in the context of the present invention for the structural units of formulas (1) and (2) refer to the total amount of all repeating structural units contained in the polymers according to the invention.

Various structural units of formula (1) and/or formula (2) can be contained in each case in a polymer according to the invention. A polymer according to the invention can for example contain several structural units of formula (1), which differ from one another for example by different counterions $Q^+$.

In the definitions D, E and F of the structural units of formula (2), methylene-oxy means —$CH_2$—O— or —O—$CH_2$—, ethylene-oxy means —$CH_2$—$CH_2$—O— or —O—$CH_2$—$CH_2$—, and propylene-oxy means —CH($CH_3$)—$CH_2$—O—, —$CH_2$—CH($CH_3$)—O—, —O—CH($CH_3$)—$CH_2$— or —O—$CH_2$—CH($CH_3$)—.

The polymers according to the invention are among other things eminently suitable as thickeners of aqueous systems and as consistency agents, especially in cosmetic, dermatological or pharmaceutical compositions. Compared to polymers from the prior art, they display in particular a more caring skin feel. Furthermore, they also bring about a higher viscosity, especially in salt-containing compositions, e.g. in water-containing salt-containing compositions. In addition, they display advantageous salt stability. Moreover, they also have an advantageous long-term care effect. Advantageously, they further display good thickening properties over a wide range of pH, i.e. even at strongly acidic pH.

In the one or more structural units of formula (1) of the polymers according to the invention, $R^a$ is preferably hydrogen or methyl and especially preferably hydrogen.

In the one or more structural units of formula (1) of the polymers according to the invention, A is preferably a structural unit of the formula —C($CH_3$)$_2$—$CH_2$—.

Especially preferably, the one or more structural units of formula (1) of the polymers of the invention is/are derived from 2-acrylamido-2-methyl-propanesulfonic acid or salts thereof.

The degree of neutralization of the one or more structural units of formula (1) of the polymers according to the invention is preferably from 50.0 to 100 mol %, more preferably from 80.0 to 100 mol %, especially preferably from 90.0 to 100 mol % and very preferably from 95.0 to 100 mol %.

In the one or more structural units of formula (1) of the polymers according to the invention, the counterion $Q^+$ that is different from $H^+$ is preferably selected from $NH_4^+$, alkali$^+$, wherein alkali$^+$ is preferably $Na^+$, ½ alkaline earth$^{++}$, wherein ½ alkaline earth$^{++}$ is preferably ½ $Ca^{++}$ and ½ $Mg^{++}$, and mixtures of these ions. Especially preferably the counterion $Q^+$ that is different from $H^+$ is selected from the group consisting of $NH_4^+$ and $Na^+$. Especially preferably the counterion $Q^+$ that is different from $H^+$ is $NH_4^+$.

In the one or more structural units of formula (2) of the polymers according to the invention, $R^1$ is preferably hydrogen, ethyl or methylol and especially preferably hydrogen or ethyl.

In the one or more structural units of formula (2) of the polymers according to the invention, $R^{2a}$, $R^{2b}$ and $R^{2c}$, in each case independently of one another, are preferably hydrogen or methyl and especially preferably hydrogen.

In the one or more structural units of formula (2) of the polymers according to the invention, X is preferably a chemical bond, methylene or ethylene and especially preferably a chemical bond or methylene.

In the one or more compounds of formula (2), $Y_1$, $Y_2$ and $Y_3$ in each case independently of one another preferably denote C(O)O, OC(O), C(O)NR$^3$ or NR$^3$C(O) and especially preferably C(O)O or OC(O).

$R^3$ is preferably hydrogen or a linear or branched alkyl residue with 1 to 10 and preferably 1 to 6 carbon atoms.

In the one or more structural units of formula (2) of the polymers according to the invention, D, E and F are, in each case independently of one another, preferably methylene-oxy, ethylene-oxy or propylene-oxy and especially preferably ethylene-oxy or propylene-oxy.

As already mentioned, a polymer according to the invention can for example contain several structural units of formula (2). These several structural units of formula (2) can for example differ from one another by the degree of ethoxylation and/or propoxylation.

Provided that in the structural units -[-D-]$_o$-, -[-E-]$_p$- and -[-F-]$_q$- of formula (2) one or more of the variable numbers o, p or q is an integer>1, the respective structural units can be constructed from a single unit or also from different units. If for example the variable number "o"=3, then the structural unit -[-D-]$_o$- can be constructed for example from 3 ethylene-oxy units. It can, however, also be constructed e.g. from 2 ethylene-oxy units and 1 propylene-oxy unit (or vice versa) or it can also be constructed e.g. from 1 methylene-oxy unit, 1 ethylene-oxy unit and 1 propylene-oxy unit, and so on. All other combinations of units within the structural units -[-D-]$_o$-, -[-E-]$_p$- and -[-F-]$_q$— are also possible, provided that the definition of the groups D, E and F and of the variable numbers o, p and q is observed. Within the structural units -[-D-]$_o$-, -[-E-]$_p$- and -[-F-]$_q$-, the distribution of the individual units can be random, alternating, gradient-like or block-like and is preferably random or block-like.

In the one or more structural units of formula (2) of the polymers according to the invention, the individual structural units -[-D-]$_o$-, -[-E-]$_p$- and -[-F-]$_q$- can, as just described, be constructed from different units. In this case the corresponding units are preferably selected from the group consisting of methylene-oxy, ethylene-oxy and propylene-oxy and especially preferably are selected from the group consisting of ethylene-oxy and propylene-oxy.

In the one or more structural units of formula (2) of the polymers according to the invention, o, p and q are, in each case independently of one another, preferably integers from 0 to 30, especially preferably integers from 0 to 15 and quite especially preferably integers from 0 to 10.

In the one or more structural units of formula (2) of the polymers according to the invention, the sum o+p+q is preferably from 3 to 90, especially preferably from 3 to 45, quite especially preferably from 3 to 30 and very preferably from 3 to 20.

The one or more crosslinking structural units of formula (2) of the polymers according to the invention are preferably derived from ethoxylated triacrylic or ethoxylated trimethacrylic acid esters, ethoxylated triacrylic or ethoxylated trimethacrylic acid amides, propoxylated triacrylic or propoxylated trimethacrylic acid esters, propoxylated triacrylic or propoxylated trimethacrylic acid amides, random or block functionalized ethoxylated/propoxylated triacrylic or random or block functionalized ethoxylated/propoxylated trimethacrylic acid esters, ethoxylated/propoxylated triacrylic or ethoxylated/propoxylated trimethacrylic acid amides, or other ethoxylated triacrylic or ethoxylated trimethacrylic acid esters, ethoxylated triacrylic or ethoxylated trimethacrylic acid amides of multifunctional alcohols, or other propoxylated triacrylic or propoxylated trimethacrylic acid esters, propoxylated triacrylic or propoxylated trimethacrylic acid amides of multifunctional alcohols, or other random or block functionalized ethoxylated/propoxylated triacrylic or ethoxylated/propoxylated trimethacrylic acid esters, ethoxylated/propoxylated triacrylic or ethoxylated/propoxylated trimethacrylic acid amides of other multifunctional alcohols, or ethoxylated glycerol triacrylates or methacrylates, or propoxylated glycerol triacrylates or methacrylates or other random or block functionalized ethoxylated/propoxylated glycerol triacrylates or methacrylates, or ethoxylated glycerol triacrylamides or methacrylamides, or propoxylated glycerol triacrylamides or methacrylamides or other random or block functionalized ethoxylated/propoxylated glycerol triacrylamides or methacrylamides, or ethoxylated trimethylolpropane triacrylates or trimethacrylates or propoxylated trimethylolpropane triacrylates or trimethacrylates or other random or block functionalized ethoxylated/propoxylated trimethylolpropane triacrylates or trimethacrylates or ethoxylated trimethylolpropane triacrylamides or trimethacrylamides or propoxylated trimethylolpropane triacrylamides or trimethacrylamides or other random or block functionalized ethoxylated/propoxylated trimethylolpropane triacrylamides or trimethacrylamides, or ethoxylated pentaerythritol triacrylates or trimethacrylates or propoxylated pentaerythritol triacrylates or trimethacrylates or other random or block functionalized ethoxylated/propoxylated pentaerythritol triacrylates or trimethacrylates or ethoxylated pentaerythritol triacrylamides or trimethacrylamides or propoxylated pentaerythritol triacrylamides or trimethacrylamides or other random or block functionalized ethoxylated/propoxylated pentaerythritol triacrylamides or trimethacrylamides.

In an especially preferred embodiment of the invention, in the one or more structural units of formula (2) $R^1$ is hydrogen or ethyl, $R^{2a}$, $R^{2b}$ and $R^{2c}$ are in each case independently of one another hydrogen or methyl, X is a chemical bond or methylene, $Y_1$, $Y_2$ and $Y_3$ are in each case independently of one another C(O)O or OC(O), D, E and F are in each case independently of one another ethylene-oxy or propylene-oxy, o, p and q are in each case independently of one another integers from 0 to 30 and the sum o+p+q is from 3 to 20.

Among these, the polymers according to the invention are in their turn preferably constructed on the basis of glycerol or on the basis of trimethylolpropane.

The following are especially preferred as crosslinking agents for the polymers according to the invention, i.e. as compounds from which the one or more structural units of formula (2) are derived:

glycerol propoxylate triacrylate (3/3 PO/OH; PO=propylene-oxy; in the synthesis, 3 mol propylene oxide was used for 3 mol OH groups of the glycerol) (GPTA),
glycerol ethoxylate triacrylate (3/3 EO/OH; EO=ethylene-oxy) (GETA),
glycerol propoxylate triacrylate (15/3 PO/OH) (GP$_{15}$TA),
glycerol ethoxylate triacrylate (15/3 EO/OH) (GE$_{15}$TA),
glycerol propoxyethoxylate triacrylate (15/3 PO-EO/OH) (GPETA),
trimethylolpropane propoxytriacrylate (3/3 PO/OH) (TMPTA-PO-3),
trimethylolpropane ethoxytriacrylate (3/3 EO/OH) (TMPTA-EO-3),
trimethylolpropane propoxytriacrylate (TMPTA-PO-6),
trimethylolpropane ethoxytriacrylate (6/3 EO/OH) (TMPTA-EO-6),
trimethylolpropane ethoxytriacrylate (15/3 EO/OH) (TMPTA-EO-15),
trimethylolpropane propoxyethoxytriacrylate (15/3 PO-EO/OH) (TMPTA-PO-EO-150)
and
trimethylolpropane ethoxypropoxytriacrylate (TMPTA-EO-PO).

The following are especially preferred:
glycerol propoxylate triacrylate (GPTA),
glycerol propoxylate triacrylate (15/3 PO/OH) (GP$_{15}$TA),
trimethylolpropane propoxytriacrylate (3/3 PO/OH) (TMPTA-PO-3),
trimethylolpropane ethoxytriacrylate (3/3 EO/OH) (TMPTA-EO-3) and
trimethylolpropane ethoxytriacrylate (15/3 EO/OH) (TMPTA-EO-15).

The following are exceptionally preferred:
glycerol propoxylate triacrylate (GPTA),
trimethylolpropane propoxytriacrylate (3/3 PO/OH) (TMPTA-PO-3) and
trimethylolpropane ethoxytriacrylate (3/3 EO/OH) (TMPTA-EO-3).

Among these compounds, glycerol propoxylate triacrylate (GPTA) is preferred.

Repeating structural units contained in polymers are derived from the polymerizable monomers used for producing them. The distribution of the various repeating structural units of formulas (1) and (2) in the polymers according to the invention can be random, block-like, alternating or gradient-like and is preferably random or gradient-like.

The proportion by weight of the repeating structural units of formulas (1) and (2) in the polymers according to the invention, relative to the total weight of all chemically bound structural units in the polymers according to the invention, is preferably greater than or equal to 85 wt %, especially preferably greater than or equal to 90 wt %, more preferably greater than or equal to 95 wt % and very preferably greater than or equal to 97 wt %. Chemically bound structural units that may be contained in the polymers according to the invention, but are not derived from the polymerizable monomers used for their production, may in particular be structural units that are derived from initiators used for producing the polymers according to the invention.

The polymers according to the invention preferably have a molecular weight from $10^3$ to $10^9$ g/mol, especially preferably from $10^4$ to $10^7$ g/mol and quite especially preferably from $10^5$ to $5 \cdot 10^6$ g/mol.

The production of the polymers according to the invention takes place by radical polymerization in a protic solvent, preferably in tert-butanol. In this case the corresponding monomers are for example dissolved or dispersed in the protic solvent and the polymerization is started in a manner that is known per se, e.g. by adding a radical-forming compound. As starter or initiator, in principle all substances known and suitable for this purpose can be used in the usual amounts. In a preferred embodiment of the invention, however, dilauroyl peroxide (DLP) or dimethyl 2,2'-azobis(2-methylpropionate) (V601) is used as initiator. The amount of initiator for producing the polymers according to the invention is preferably less than or equal to 10 wt %, especially preferably less than or equal to 5 wt % and quite especially preferably less than or equal to 3 wt %, relative to the total amount of monomers and initiator used for the polymerization. The monomers used can for example be polymerized "directly". However, they can also be neutralized before polymerization, for example by reacting acid groups of the monomers used with bases before polymerization. Instead of neutralizing the monomers before polymerization, however, the polymers can also be neutralized with the bases after completion of polymerization.

The present invention therefore further relates to a method of producing the polymers according to the invention, wherein monomers, from which the structural units of formula (1) and formula (2) are derived, undergo radical polymerization in a protic solvent, preferably in tert-butanol, and optionally the monomers before polymerization, or the polymer after polymerization, are neutralized with ammonia or organic amines or an alkali$^+$-containing, preferably an Li$^+$-, Na$^+$- or K$^+$-containing, an alkaline-earth$^{++}$-containing, preferably a Ca$^{++}$- or Mg$^{++}$-containing, or a Zn$^{++}$- or Al$^{+++}$-containing base. If neutralization is carried out with alkali$^+$, alkaline-earth$^{++}$, Zn$^{++}$- or Al$^{+++}$-containing bases, in a preferred embodiment it is carried out with the corresponding hydroxides or carbonates and in an especially preferred embodiment with hydroxides.

Radical polymerizations are generally known by a person skilled in the art and are described in detail in standard works, e.g. in "Makromolekulare Chemie: Eine Einführung" [Macromolecular chemistry: An introduction] by Bernd Tieke, Wiley-VCH, 2nd completely revised and enlarged edition (9 Sep. 2005) ISBN-10: 3527313796.

The polymers according to the invention are characterized by good mildness on the skin and a pleasant, rich skin feel. They also possess advantageous thickening properties especially in salt-containing compositions, e.g. in water-containing salt-containing compositions, and high electrolyte stability. Furthermore, the polymers according to the invention are acid-stable. As the polymers according to the invention thicken even at acidic pH, thickened cosmetic, dermatological or pharmaceutical products can advantageously also be preserved with organic acids, such as benzoic acid, sorbic acid, paramethoxybenzoic acid, as sufficient thickener performance is available even at the required low pH. Clear solutions can be obtained with them.

The polymers according to the invention are advantageously suitable for producing cosmetic, dermatological or pharmaceutical compositions.

The present invention therefore further relates to the use of one or more polymers according to the invention for producing cosmetic, dermatological or pharmaceutical compositions and to cosmetic, dermatological or pharmaceutical compositions containing one or more polymers according to the invention.

The cosmetic, dermatological or pharmaceutical compositions according to the invention contain the one or more polymers according to the invention preferably in an amount from 0.01 to 10.0 wt %, especially preferably in an amount from 0.1 to 5.0 wt % and quite especially preferably in an amount from 0.25 to 2.0 wt %, in each case relative to the total weight of the compositions according to the invention.

In a preferred embodiment of the invention the cosmetic, dermatological or pharmaceutical compositions according to the invention have viscosities preferably in the range from 100 to 200 000 mPa·s, especially preferably in the range from 1 000 to 100 000 mPa·s, quite especially preferably in the range from 2000 to 50 000 mPa·s and very preferably in the range from 5000 to 30 000 mPa·s (25° C., Brookfield RVT, T-C spindle at 20 revolutions per minute).

In another preferred embodiment of the invention the compositions according to the invention are in the form of fluids, gels, foams, sprays, lotions or creams.

The compositions according to the invention are preferably constructed on an aqueous or aqueous-alcoholic basis or are in the form of emulsions, preferably in the form of oil-in-water emulsions.

In an especially preferred embodiment of the invention the compositions according to the invention are in the form of aqueous-alcoholic compositions and preferably contain, relative to the total weight of the compositions,
a) up to 90.0 wt %, preferably 19.49 to 80.0 wt %, especially preferably 23.9 to 70.0 wt %, quite especially preferably 28.5 to 60.0 wt % water,
b) up to 90.0 wt %, preferably 19.49 to 80.0 wt %, especially preferably 28.9 to 75.0 wt %, quite especially preferably 38.5 to 70.0 wt % of one or more alcohols, preferably ethanol or isopropanol,
c) up to 10.0 wt %, preferably 0.01 to 10.0 wt %, especially preferably 0.1 to 5.0 wt %, quite especially preferably 0.5 to 2.0 wt % of one or more of the polymers according to the invention and
d) up to 20.0 wt %, preferably 0.5 to 10.0 wt %, especially preferably 1.0 to 5.0 wt %, quite especially preferably 1.0 to 3.0 wt % of one or more further additives.

The one or the several further additives in the aqueous-alcoholic compositions just mentioned is/are preferably selected from the group consisting of surfactants and antimicrobial active substances. In a preferred embodiment of the invention, for example as in the case just mentioned, the compositions according to the invention are in the form of disinfectant gels.

In another especially preferred embodiment of the invention the compositions according to the invention are in the form of oil-in-water emulsions and preferably contain, relative to the total weight of the compositions,
a) up to 95.0 wt %, preferably 49.49 to 95.0 wt %, especially preferably 68.9 to 90.0 wt %, quite especially preferably 70.0 to 85.0 wt % of an aqueous phase or aqueous-alcoholic phase,
b) up to 70.0 wt %, preferably 4.49 to 50.0 wt %, especially preferably 8.9 to 30.0 wt %, quite especially preferably 13.5 to 25.0 wt % of an oily phase,
c) up to 10.0 wt %, preferably 0.01 to 10.0 wt %, especially preferably 0.1 to 5.0 wt %, quite especially preferably 0.5 to 2.0 wt % of one or more of the polymers according to the invention and
d) up to 20.0 wt %, preferably 0.5 to 10 wt %, especially preferably 1.0 to 5.0 wt %, especially preferably 1.0 to 3.0 wt % of one or more further additives.

The one or the several further additives in the oil-in-water emulsions just mentioned is/are preferably selected from the group consisting of emulsifiers, coemulsifiers, solubilizers, active substances, sunscreen filters, pigments and antimicrobial active substances.

For the compositions according to the invention with aqueous-alcoholic or also alcoholic basis, consideration may be given to all mono- or polyhydric alcohols. Alcohols with 1 to 4 carbon atoms such as ethanol, propanol, isopropanol, n-butanol, i-butanol, tert-butanol or glycerol and alkylene glycols, especially propylene, butylene or hexylene glycol, and mixtures of the aforesaid alcohols are preferably used. Further preferred alcohols are polyethylene glycols with a relative molecular weight below 2000. Use of ethanol or isopropanol is especially preferred.

The compositions according to the invention can contain one or more oils.

The oils can advantageously be selected from the groups of triglycerides, natural and synthetic fats, preferably esters of fatty acids with alcohols with a low number of carbons, e.g. with methanol, isopropanol, propylene glycol or glycerol, or esters of fatty alcohols with alkanoic acids with a low number of carbons or with fatty acids or from the group of alkyl benzoates, as well as natural or synthetic hydrocarbon oils.

Consideration may be given to triglycerides of linear or branched, saturated or unsaturated, optionally hydroxylated, $C_8$-$C_{30}$-fatty acids, especially vegetable oils, such as sunflower oil, corn oil, soybean oil, rice oil, jojoba oil, babusscu oil, pumpkin oil, grapeseed oil, sesame oil, walnut oil, apricot oil, orange oil, wheat germ oil, peach kernel oil, macadamia oil, avocado oil, sweet almond oil, lady's smock oil, castor oil, olive oil, peanut oil, rape oil and coconut oil, and synthetic triglyceride oils, e.g. the commercial product Myritol® 318. Hardened triglycerides are also preferred according to the invention. Also oils of animal origin, for example beef tallow, perhydrosqualene, lanolin can also be used.

Another class of preferred oils are the benzoic acid esters of linear or branched $C_{8-22}$ alkanols, e.g. the commercial products Finsolv®SB (isostearyl benzoate), Finsolv®TN ($C_{12}$-$C_{15}$ alkyl benzoate) and Finsol® EB (ethylhexyl benzoate).

Another class of preferred oils are the dialkyl ethers with a total of 12 to 36 carbon atoms, especially with 12 to 24 carbon atoms, e.g. di-n-octyl ether (Cetiol® OE), di-n-nonyl ether, di-n-decyl ether, di-n-undecyl ether, di-n-dodecyl ether, n-hexyl-n-octyl ether, n-octyl-n-decyl ether, n-decyl-n-undecyl ether, n-undecyl-n-dodecyl ether and n-hexyl-n-undecyl ether, di-3-ethyldecyl ether, tert-butyl-n-octyl ether, iso-pentyl-n-octyl ether and 2-methylpentyl-n-octyl ether and di-tert-butyl ether and diisopentyl ether.

Consideration may also be given to branched saturated or unsaturated fatty alcohols with 6-30 carbon atoms, e.g. isostearyl alcohol, and Guerbet alcohols.

Another class of preferred oils are hydroxycarboxylic acid alkyl esters. Preferred hydroxycarboxylic acid alkyl esters are full esters of glycolic acid, lactic acid, malic acid, tartaric acid or citric acid. Other basically suitable esters of hydroxycarboxylic acids are esters of β-hydroxypropionic acid, of tartronic acid, of D-gluconic acid, sugar acid, mucic acid or glucuronic acid. Primary, linear or branched aliphatic alcohols with 8 to 22 carbon atoms are suitable as the alcohol component of these esters. Moreover, the esters of $C_{12}$-$C_{15}$ fatty alcohols are especially preferred. Esters of this type are available commercially, e.g. under the trade name Cosmacol® from EniChem, Augusta Industriale.

Another class of preferred oils are dicarboxylic acid esters of linear or branched $C_2$-$C_{10}$ alkanols, such as di-n-butyladipate (Cetiol® B), di-(2-ethylhexyl)adipate and di-(2-ethylhexyl)succinate and diol esters such as ethylene glycol dioleate, ethylene glycol diisotridecanoate, propylene glycol di-(2-ethylhexanoate), propylene glycol diisostearate, propylene glycol dipelargonate, butanediol-diisostearate and neopentyl glycol dicaprylate and diisotridecylacelaat.

Oils that are also preferred are symmetric, asymmetric or cyclic esters of carbonic acid with fatty alcohols, glycerol carbonate or dicaprylyl carbonate (Cetiol® CC).

Another class of preferred oils are the esters of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols.

Another class of preferred oils are hydrocarbon oils, for example those with linear or branched, saturated or unsaturated $C_7$-$C_{40}$ carbon chains, for example petroleum jelly, dodecane, isododecane, cholesterol, lanolin, synthetic hydrocarbons such as polyolefins, especially polyisobutene, hydrogenated polyisobutene, polydecane, and hexadecane, isohexadecane, paraffin oils, isoparaffin oils, e.g. the commercial products of the Permethyl® series, squalane, squalene, and alicyclic hydrocarbons, e.g. the commercial product 1,3-di-(2-ethylhexyl)-cyclohexane (Cetiol® S), ozokerite, and ceresin.

Consideration may also be given to silicone oils or waxes, preferably dimethylpolysiloxanes and cyclomethicones, polydialkylsiloxanes $R_3SiO(R_2SiO)_xSiR_3$, wherein R stands for methyl or ethyl, especially preferably for methyl, and x stands for a number from 2 to 500, for example the dimethicones obtainable under the trade names VICASIL (General Electric Company), DOW CORNING 200, DOW CORNING 225, DOW CORNING 200 (Dow Corning Corporation), and the dimethicones obtainable as SilCare® Silicone 41M65, SilCare® Silicone 41M70, SilCare®Silicone 41M80 (Clariant), stearyldimethylpolysiloxane, $C_{20}$-$C_{24}$ alkyl-dimethylpolysiloxane, $C_{24}$-$C_{28}$ alkyl-dimethylpolysiloxane, but also the methicones obtainable as SilCare® Silicone 41M40, SilCare® Silicone 41M50 (Clariant), furthermore trimethylsiloxysilicates $[(CH_2)_3SiO)_{1/2}]_x$ $[SiO_2]_y$, where x stands for a number from 1 to 500 and y for a number from 1 to 500, dimethiconols $R_3SiO$ $[R_2SiO]_xSiR_2OH$ and $HOR_2SiO[R_2SiO]_xSiR_2OH$, where R stands for methyl or ethyl and x for a number up to 500, polyalkylarylsiloxanes, for example the polymethylphenylsiloxanes obtainable under the trade names SF 1075 METHYLPHENYL FLUID (General Electric Company) and 556 COSMETIC GRADE PHENYL TRIMETHICONE FLUID (Dow Corning Corporation), polydiarylsiloxanes, silicone resins, cyclic silicones and amino-, fatty acid-, alcohol-, polyether-, epoxy-, fluoro- and/or alkyl-modified silicone compounds, and polyethersiloxane copolymers.

The compositions according to the invention can contain, as further auxiliaries and additives, for example waxes, emulsifiers, coemulsifiers, solubilizers, electrolytes, hydroxy acids, stabilizers, cationic polymers, film formers, further thickeners, gelling agents, overfatting agents, refatting agents, antimicrobial active substances, biogenic active substances, astringents, deodorizing substances, sunscreen filters, antioxidants, humectants, solvents, colorants, nacreous agents, odorants, opacifiers and/or silicones.

The compositions according to the invention can contain waxes, for example paraffin waxes, microwaxes and ozokerites, beeswax and partial fractions thereof and beeswax derivatives, waxes from the group of homopolymeric polyethylenes or copolymers of α-olefins, as well as natural waxes such as rice wax, candelilla wax, carnauba wax, japan wax or shellac wax.

Non-ionic, anionic, cationic or amphoteric surface active compounds can be used as emulsifiers, coemulsifiers and solubilizers.

As nonionogenic surface active compounds, consideration may preferably be given to:

Addition products of 0 to 30 mol ethylene oxide and/or 0 to 5 mol propylene oxide on linear fatty alcohols with 8 to 22 carbon atoms, on fatty acids with 12 to 22 carbon atoms, on alkyl phenols with 8 to 15 carbon atoms in the alkyl group and on sorbitan or sorbitol esters; ($C_{12}$-$C_{18}$)-fatty acid mono- and diesters of addition products of 0 to 30 mol ethylene oxide on glycerol; glycerol mono- and diesters and sorbitan mono- and diesters of saturated and unsaturated fatty acids with 6 to 22 carbon atoms and optionally their ethylene oxide addition products; addition products of 15 to 60 mol ethylene oxide on castor oil and/or hardened castor oil; polyol and especially polyglycerol esters, e.g. polyglycerol polyricinoleate and polyglycerol poly-12-hydroxystearate. Ethoxylated fatty amines, fatty acid amides, fatty acid alkanolamides and mixtures of compounds from several of these classes of substances are also preferably suitable.

Suitable ionogenic coemulsifiers are e.g. anionic emulsifiers, such as mono-, di- or triphosphoric acid esters, soaps (e.g. sodium stearate), fatty alcohol sulfates as well as cationic emulsifiers such as mono-, di- and tri-alkyl quats and polymeric derivatives thereof.

Amphoteric emulsifiers that are available are preferably alkyl aminoalkyl carboxylic acids, betaines, sulfobetaines and imidazoline derivatives.

Fatty alcohol ethoxylates are used especially preferably, selected from the group of ethoxylated stearyl alcohols, isostearyl alcohols, cetyl alcohols, isocetyl alcohols, oleyl alcohols, lauryl alcohols, isolauryl alcohols and cetylstearyl alcohols, especially polyethylene glycol (13) stearyl ether, polyethylene glycol (14) stearyl ether, polyethylene glycol (15) stearyl ether, polyethylene glycol (16) stearyl ether, polyethylene glycol (17) stearyl ether, polyethylene glycol (18) stearyl ether, polyethylene glycol (19) stearyl ether, polyethylene glycol (20) stearyl ether, polyethylene glycol (12) isostearyl ether, polyethylene glycol (13) isostearyl ether, polyethylene glycol (14) isostearyl ether, polyethylene glycol (15) isostearyl ether, polyethylene glycol (16) isostearyl ether, polyethylene glycol (17) isostearyl ether, polyethylene glycol (18) isostearyl ether, polyethylene glycol (19) isostearyl ether, polyethylene glycol (20) isostearyl ether, polyethylene glycol (13) cetyl ether, polyethylene glycol (14) cetyl ether, polyethylene glycol (15) cetyl ether, polyethylene glycol (16) cetyl ether, polyethylene glycol (17) cetyl ether, polyethylene glycol (18) cetyl ether, polyethylene glycol (19) cetyl ether, polyethylene glycol (20) cetyl ether, polyethylene glycol (13) isocetyl ether, polyethylene glycol (14) isocetyl ether, polyethylene glycol (15) isocetyl ether, polyethylene glycol (16) isocetyl ether, polyethylene glycol (17) isocetyl ether, polyethylene glycol (18) isocetyl ether, polyethylene glycol (19) isocetyl ether, polyethylene glycol (20) isocetyl ether, polyethylene glycol (12) oleyl ether, polyethylene glycol (13) oleyl ether, polyethylene glycol (14) oleyl ether, polyethylene glycol (15) oleyl ether, polyethylene glycol (12) lauryl ether, polyethylene glycol (12) isolauryl ether, polyethylene glycol (13) cetylstearyl ether, polyethylene glycol (14) cetylstearyl ether, polyethylene glycol (15) cetylstearyl ether, polyethylene glycol (16) cetylstearyl ether, polyethylene glycol (17) cetylstearyl ether, polyethylene glycol (18) cetylstearyl ether, polyethylene glycol (19) cetylstearyl ether.

Fatty acid ethoxylates are also preferred, selected from the group of ethoxylated stearates, isostearates and oleates, especially polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

Sodium laureth-1'-carboxylate can be used advantageously as ethoxylated alkyl ether carboxylic acid or salts thereof.

Polyethylene glycol (60) evening primrose glycerides can be used advantageously as ethoxylated triglycerides.

Furthermore, it is advantageous to select the polyethylene glycol glycerol fatty acid ester from the group polyethylene glycol (20) glyceryl laurate, polyethylene glycol (6) glyceryl caprate/caprinate, polyethylene glycol (20) glyceryl oleate, polyethylene glycol (20) glyceryl isostearate and polyethylene glycol (18) glyceryl oleate/cocoate.

Among the sorbitan esters, the following are especially suitable:
polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Especially advantageous coemulsifiers are glyceryl monostearate, glyceryl monooleate, diglyceryl monostearate, glyceryl isostearate, polyglyceryl-3-oleate, polyglyceryl-3-diisostearate, polyglyceryl-4-isostearate, polyglyceryl-2-dipolyhydroxystearate, polyglyceryl-4-dipolyhydroxystearate, PEG-30-dipolyhydroxystearate, diisostearoylpolyglyceryl-3-diisostearate, glycol distearate and polyglyceryl-3-dipolyhydroxystearate, sorbitan monoisostearate, sorbitan stearate, sorbitan oleate, sucrose distearate, lecithin, PEG-7-hydrogenated castor oil, cetyl alcohol, stearyl alcohol, behenyl alcohol, isobehenyl alcohol and polyethylene glycol (2) stearyl ether (Steareth-2), alkyl methicone copolyols and alkyl dimethicone copolyols, especially cetyldimethicone copolyol (ABIL® EM 90), laurylmethicone copolyol or amodimethicone glycerocarbamate (SilCare® Silicone WSI, Clariant).

If the compositions according to the invention contain one or more substances selected from the group consisting of emulsifiers, coemulsifiers and solubilizers, this one or these several substances is/are contained in the compositions according to the invention preferably in an amount from 0.1 to 20.0 wt %, especially preferably in an amount from 0.5 to 10.0 wt % and quite especially preferably in an amount from 1.0 to 5.0 wt %, relative to the total weight of the corresponding composition according to the invention.

Inorganic salts can be used as electrolytes, preferably ammonium or metal salts, especially preferably halides, for example $CaCl_2$, $MgCl_2$, LiCl, KCl and NaCl, carbonates, hydrogen carbonates, phosphates, sulfates, nitrates, especially preferably sodium chloride, and/or organic salts, preferably ammonium or metal salts, especially preferably of glycolic acid, lactic acid, citric acid, tartaric acid, mandelic acid, salicylic acid, ascorbic acid, pyruvic acid, fumaric acid, retinoic acid, sulfonic acids, benzoic acid, kojic acid, fruit acid, malic acid, gluconic acid or galacturonic acid.

These also include aluminum salts, preferably aluminum hydrochloride or aluminum-zirconium complex salts.

In a preferred embodiment of the invention the compositions according to the invention therefore contain one or more substances selected from inorganic and organic salts.

As electrolyte, the compositions according to the invention can also contain mixtures of various salts.

If the compositions according to the invention contain one or more electrolytes, these are contained in the compositions according to the invention preferably in an amount from 0.01 to 20.0 wt %, especially preferably in an amount from 0.1 to 10.0 wt % and quite especially preferably in an amount from 0.5 to 5.0 wt % relative to the total weight of the corresponding composition according to the invention.

The polymers according to the invention are acid-stable and are preferably suitable for use in cosmetic, pharmaceutical and/or dermatological compositions with low pH from 2 to 6, especially preferably for products for hand and skin disinfection and for skin care.

The use of acidic additives and salts thereof sometimes makes it necessary to set the pH of the cosmetic or dermatological compositions in a definitively acidic range.

In another preferred embodiment of the invention, the compositions according to the invention contain one or more hydroxy acids, especially preferably one or more substances selected from alpha- and beta-hydroxy acids.

The compositions according to the invention can contain, as hydroxy acids, preferably lactic acid, glycolic acid, salicylic acid and alkylated salicylic acids or citric acid. Furthermore, formulations according to the invention can contain other acidic components. Consideration may be given to the following as active ingredient: tartaric acid, mandelic acid, caffeic acid, pyruvic acid, oligo-oxa mono- and dicarboxylic acids, fumaric acid, retinoic acid, sulfonic acids, benzoic acid, kojic acid, fruit acid, malic acid, gluconic acid, pyruvic acid, galacturonic acid, ribonic acid, and all derivatives thereof, polyglycol diacids in free or partial neutralized form, vitamin C (ascorbic acid), vitamin C derivatives, dihydroxyacetone or skin-whitening actives such as arbutin or glycyrrhetic acid and salts thereof. If the compositions according to the invention contain one or more of the aforementioned substances, this one or these several substances are preferably contained in the compositions according to the invention in an amount from 0.1 to 20.0 wt %, especially preferably in an amount from 0.2 to 10.0 wt % and quite especially preferably in an amount from 0.5 to 5.0 wt %, relative to the total weight of the corresponding composition according to the invention.

In another preferred embodiment of the invention, the compositions according to the invention therefore contain one or more substances selected from vitamin C and vitamin C derivatives, wherein the vitamin C derivatives are preferably selected from sodium ascorbyl phosphate, magnesium ascorbyl phosphate and magnesium ascorbyl glucoside.

In another preferred embodiment of the invention, the compositions according to the invention contain one or more substances selected from benzoic acid, sorbic acid, salicylic acid, lactic acid and paramethoxybenzoic acid. Because the polymers according to the invention also thicken in the acidic pH range and develop a flow point, it is possible to work with the aforementioned organic acids as preservatives.

In addition to the polymers according to the invention, metal salts of fatty acids, e.g. magnesium, aluminum and/or zinc stearate can be used as additional stabilizers. If the compositions according to the invention contain one or more of these aforementioned substances, this one or these several substances is/are contained in the compositions according to the invention preferably in an amount from 0.1 to 10.0 wt %, especially preferably in an amount from 0.5 to 8.0 wt % and quite especially preferably in an amount from 1.0 to 5.0 wt %, relative to the total weight of the corresponding composition according to the invention.

The substances known by the INCI designation "polyquaternium" are suitable as cationic polymers, especially polyquaternium-31, polyquaternium-16, polyquaternium-24, polyquaternium-7, polyquaternium-22, polyquaternium-39, polyquaternium-28, polyquaternium-2, polyquaternium-10, polyquaternium-11, and polyquaternium 37&mineral oil&PPG trideceth (Salcare SC95), PVP-dimethylaminoethylmethacrylate copolymer, guar hydroxypropyltriammonium chloride, and calcium alginate and ammonium alginate. Moreover, it is possible to use cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethylenimines; cationic silicone polymers, e.g. amidomethicones; copolymers of adipic acid and dimethylaminohydroxypropyl diethylenetriamine; polyaminopolyamide and cationic chitin derivatives, for example chitosan.

If the compositions according to the invention contain one or more of the aforementioned cationic polymers, these are contained in the compositions according to the invention preferably in an amount from 0.1 to 5.0 wt %, especially preferably in an amount from 0.2 to 3.0 wt % and quite especially preferably in an amount from 0.5 to 2.0 wt %, relative to the total weight of the corresponding composition according to the invention.

Moreover, the compositions according to the invention can contain film formers, which are, depending on the intended use, selected from salts of phenylbenzimidazole sulfonic acid, water-soluble polyurethanes, for example $C_{10}$-polycarbamyl polyglyceryl ester, polyvinyl alcohol, polyvinylpyrrolidone copolymers, for example vinylpyrrolidone/vinyl acetate copolymer or PVP/eicosene copolymers, maleinized polypropylene polymers, water-soluble acrylic acid polymers/copolymers or esters or salts thereof, for example partial-ester copolymers of acrylic/methacrylic acid, water-soluble cellulose, for example hydroxymethylcellulose, hydroxyethylcellulose, hydroxypropylcellulose, water-soluble quaterniums, polyquaterniums, carboxyvinyl polymers, such as carbomers and salts thereof, polysaccharides, for example polydextrose and glucan, vinyl acetate/crotonate, available for example under the trade name Aristoflex® A 60 (Clariant).

If the compositions according to the invention contain one or more film formers, these are contained in the compositions according to the invention preferably in an amount from 0.1 to 10.0 wt %, especially preferably in an amount from 0.2 to 5.0 wt % and quite especially preferably in an amount from 0.5 to 3.0 wt %, relative to the total weight of the corresponding composition according to the invention.

The desired viscosity of the compositions can be adjusted by adding further thickeners and gelling agents. Consideration may preferably be given to cellulose ethers and other cellulose derivatives (e.g. carboxymethylcellulose, hydroxyethylcellulose), gelatin, starch and starch derivatives, sodium alginates, fatty acid polyethylene glycol esters, agar-agar, carrageenan, tragacanth or dextrin derivatives, especially dextrin esters. Moreover, metal salts of fatty acids are suitable, preferably with 12 to 22 carbon atoms, for example sodium stearate, sodium palmitate, sodium laurate, sodium arachidate, sodium behenate, potassium stearate, potassium palmitate, sodium myristate, aluminum monostearate, hydroxy fatty acids, for example 12-hydroxystearic acid, 16-hydroxyhexadecanoylic acid; fatty acid amides; fatty acid alkanolamides; dibenzalsorbitol and alcohol-soluble polyamides and polyacrylamides or mixtures thereof. Furthermore, crosslinked and non-crosslinked polyacrylates such as carbomers, sodium polyacrylates or sulfonic acid-containing polymers such as ammonium acryloyl dimethyltaurate/VP copolymer or sodium acryloyl dimethyltaurate/VP copolymer can be used.

If the compositions according to the invention contain one or more substances selected from the group consisting of thickeners and gelling agents, this one or these several substances is/are contained in the compositions according to the invention preferably in an amount from 0.01 to 20.0 wt %, especially preferably in an amount from 0.1 to 10.0 wt %, quite especially preferably in an amount from 0.2 to 3.0 wt % and very preferably in an amount from 0.4 to 2.0 wt %, relative to the total weight of the corresponding composition according to the invention.

Lanolin and lecithin, non-ethoxylated and polyethoxylated or acylated lanolin and lecithin derivatives, polyol fatty acid esters such as glyceryl oleate, mono-, di- and triglycerides and/or fatty acid alkanolamides, wherein the latter serve simultaneously as foam stabilizers, can preferably be used as overfatting agents or refatting agents. If the compositions according to the invention contain one or more of the substances just mentioned, this one or these several substances is/are contained in the compositions according to the invention preferably in an amount from 0.01 to 10.0 wt %, especially preferably in an amount from 0.1 to 5.0 wt % and quite especially preferably in an amount from 0.5 to 3.0 wt %, relative to the total weight of the corresponding composition according to the invention.

In another preferred embodiment of the invention, the compositions according to the invention contain one or more antimicrobial active substances and are preferably in the form of disinfection compositions and especially preferably in the form of disinfectant gels.

The following can be used as antimicrobial active substances: cetyltrimethylammonium chloride, cetylpyridinium chloride, benzethonium chloride, diisobutylethoxyethyl dimethylbenzylammonium chloride, sodium N-laurylsarcosinate, sodium N-palmethylsarcosinate, lauroylsarcosine, N-myristoylglycine, potassium N-laurylsarcosine, trimethylammonium chloride, sodium aluminum chlorohydroxylactate, triethyl citrate, tricetyl methylammonium chloride, 2,4,4'-trichloro-2'-hydroxydiphenyl ether (triclosan), phenoxyethanol, 1,5-pentanediol, 1,6-hexanediol, 3,4,4'-trichlorocarbanilide (triclocarban), diaminoalkyl amide, for example L-lysine-hexadecyl amide, citrate heavy-metal salts, salicylates, piroctoses, especially zinc salts, pyrithiones and heavy-metal salts thereof, especially zinc pyrithione, zinc phenolsulfate, farnesol, ketoconazole, oxiconazole, bifonazole, butoconazole, cloconazole, clotrimazole, econazole, enilconazole, fenticonazole, isoconazole, miconazole, sulconazole, thioconazole, fluconazole, itraconazole, terconazole, naftifine and terbinafine, selenium disulfide and Octopirox®, iodopropynylbutyl carbamate, methylchloroisothiazolinone, methylisothiazolinone, methyldibromoglutaronitrile, AgCl, chloroxylenol, Na salt of diethylhexylsulfosuccinate, sodium benzoate, and phenoxyethanol, benzyl alcohol, phenoxyisopropanol, parabens, preferably butyl-, ethyl-, methyl- and propylparaben, and Na salts thereof, pentanediol 1,2-octanediol, 2-bromo-2-nitropropane-1,3-diol, ethylhexylglycerol, benzyl alcohol, sorbic acid, benzoic acid, lactic acid, imidazolidinylurea, diazolidinylurea, dimethylol dimethylhydantoin (DMDMH), Na salt of hydroxymethyl glycinate, hydroxyethylglycine of sorbic acid and combinations of these active ingredients.

If the compositions according to the invention contain one or more antimicrobial active substances, these are contained in the compositions according to the invention preferably in an amount from 0.001 to 5.0 wt %, especially preferably in an amount from 0.01 to 3.0 wt % and quite especially preferably in an amount from 0.1 to 2.0 wt %, relative to the total weight of the corresponding composition according to the invention.

The compositions according to the invention can in addition contain biogenic active substances, selected from plant extracts, for example Aloe vera, and local anesthetics, antibiotics, antiphlogistics, antiallergic agents, corticosteroids, sebostatics, Bisabolol®, allantoin, Phytantriol®, proteins, vitamins selected from niacin, biotin, vitamin B2, vitamin B3, vitamin B6, vitamin B3 derivatives (salts, acids, esters, amides, alcohols), vitamin C and vitamin C derivatives (salts, acids, esters, amides, alcohols), preferably as sodium salt of the monophosphoric acid ester of ascorbic acid or as magnesium salt of the phosphoric acid ester of ascorbic acid, tocopherol and tocopherol acetate, and vitamin E and/or its derivatives.

If the compositions according to the invention contain one or more biogenic active substances, these are contained in the compositions according to the invention preferably in an amount from 0.001 to 5.0 wt %, especially preferably in an amount from 0.01 to 3.0 wt % and quite especially preferably in an amount from 0.1 to 2.0 wt %, relative to the total weight of the corresponding composition according to the invention.

The compositions according to the invention can contain astringents, preferably magnesium oxide, aluminum oxide, titanium dioxide, zirconium dioxide and zinc oxide, oxide hydrates, preferably aluminum oxide hydrate (boehmite) and hydroxides, preferably of calcium, magnesium, aluminum, titanium, zirconium or zinc, and aluminum hydrochlorides. If the compositions according to the invention contain one or more astringents, these are contained in the compositions according to the invention preferably in an amount from 0.001 to 50.0 wt %, especially preferably in an amount from 0.01 to 10.0 wt % and quite especially preferably in an amount from 0.1 to 10.0 wt %, relative to the total weight of the corresponding composition according to the invention.

Allantoin and Bisabolol are preferred as deodorizing substances. If the compositions according to the invention contain one or more deodorizing substances, these are contained in the compositions according to the invention preferably in an amount from 0.0001 to 10.0 wt %, relative to the total weight of the corresponding composition according to the invention.

In another preferred embodiment of the invention, the compositions according to the invention contain one or more substances selected from inorganic and organic UV filters and especially preferably are in the form of sunscreen compositions.

The compositions according to the invention can contain microfine titanium dioxide, mica-titanium oxide, iron oxides, mica-iron oxide, zinc oxide, silicon oxides, ultramarine blue or chromium oxides as pigments/micropigments and as inorganic sunscreen filters or UV filters.

The organic sunscreen filters or UV filters are preferably selected from 4-aminobenzoic acid, 3-(4'-trimethylammonium)-benzylidene-bornan-2-one-methylsulfate, camphor benzalkonium methosulfate, 3,3,5-trimethyl-cyclohexylsalicylate, 2-hydroxy-4-methoxybenzophenone, 2-phenylbenzimidazole-5-sulfonic acid and their potassium, sodium and triethanolamine salts, 3,3'-(1,4-phenylenedimethine)-bis(7,7-dimethyl-2-oxobicyclo[2.2.1]-heptane-1-methanesulfonic acid) and salts thereof, 1-(4-tert-butylphenyl)-3-(4-methoxyphenyl)propane-1,3-dione, 3-(4'-sulfo)-benzylidene-bornan-2-one and salts thereof, 2-cyano-3,3-diphenylacrylic acid-(2-ethylhexyl ester), polymers of N-[2(and 4)-(2-oxoborn-3-ylidenemethyl)benzyl]-acrylamide, 4-methoxy-cinnamic acid-2-ethylhexyl ester, ethoxylated ethyl-4-aminobenzoate, 4-methoxy-cinnamic acid isoamyl ester, 2,4,6-tris-[p-(2-ethylhexyloxycarbonyl)anilino]-1,3,5- triazine, 2-(2H-benzotriazol-2-yl)-4-methyl-6-(2-methyl-3-(1,3,3,3-tetramethyl-1-(trimethylsilyloxy)-disiloxanyl)-propyl)phenol, 4,4'-[(6-[4-((1,1-dimethylethyl)-aminocarbonyl)phenylamino]-1,3,5-triazin-2,4-yl)diimino] bis-(benzoic acid-2-ethylhexyl ester), benzophenone-3, benzophenone-4 (acid), 3-(4'-methylbenzylidene)-D,L-camphor, 3-benzylidene-camphor, salicylic acid-2-ethylhexyl ester, 4-dimethylaminobenzoic acid-2-ethylhexyl ester, hydroxy-4-methoxy-benzophenone-5-sulfonic acid (sulfisobenzonum) and the sodium salt, 4-isopropylbenzyl-salicylate, N,N,N-trimethyl-4-(2-oxoborn-3-ylidenemethyl) anilium methyl sulfate, homosalate (INN), oxybenzone (INN), 2-phenylbenzimidazole-5-sulfonic acid and their sodium, potassium, and triethanolamine salts, octyl-methoxycinnamic acid, isopentyl-4-methoxycinnamic acid, isoamyl-p-methoxycinnamic acid, 2,4,6-trianilino-(p-carbo-2'-ethylhexyl-1'-oxy)-1,3,5-triazine (octyl triazone) phenol, 2-2(2H-benzotriazol-2-yl)-4-methyl-6-(2-methyl-3-(1,3,3,3-tetramethyl-1-(trimethylsilypoxy)-disiloxanyl)propyl (drometrizole trisiloxane) benzoic acid, 4,4-((6-(((1,1-dimethylethyl)amino)carbonyl)phenyl)amino)-1,3,5-triazine-2,4-diyl)diimino)bis,bis(2-ethylhexyl)ester) benzoic acid, 4,4-((6-(((1,1-dimethylethyl)amino)-carbonyl)phenyl)amino)-1,3,5-triazine-2,4-diyl)diimino)bis,bis(2-ethylhexyl)ester), 3-(4'-methylbenzylidene)-D, L-camphor (4-methylben-zylidene camphor), benzylidene-camphor-sulfonic acid, octocrylene, polyacrylamidomethyl-benzylidene-camphor, 2-ethylhexyl salicylate (octyl salicylate), 4-dimethyl-aminobenzoic acid ethyl-2-hexyl ester (octyl dimethyl PABA), PEG-25 PABA, 2-hydroxy-4-methoxybenzophenone-5-sulfonic acid (benzophenone-5) and the Na salt, 2,2'-methylene-bis-6-(2H-benzotriazol-2-yl)-4-(tetramethylbutyl)-1,1,3,3-phenol, sodium salt of 2-2'-bis-(1,4-phenylene)1H-benzimidazole-4,6-disulfonic acid, (1,3,5)-triazine-2,4-bis((4-(2-ethylhexyloxy)-2-hydroxy)-phenyl)-6-(4-methoxyphenyl), 2-ethylhexyl-2-cyano-3,3-diphenyl-2-propenoate, glyceryl octanoate, di-p-methoxycinnamic acid, p-amino-benzoic acid and esters thereof, 4-tert-butyl-4'-methoxydibenzoylmethane, 4-(2-β-glucopyranoxy) propoxy-2-hydroxybenzophenone, octyl salicylate, methyl-2,5-diisopropylcinnamic acid, cinoxate, dihydroxy-dimethoxybenzophenone, disodium salt of 2,2'-dihydroxy-4,4'-dimethoxy-5,5'-disulfobenzophenone, dihydroxybenzophenone, 1,3,4-dimethoxwhenyl-4,4-dimethyl-1,3-pentanedione, 2-ethylhexyl-dimethoxyben-zylidene-dioxoimidazolidine propionate, methylene-bis-benzotriazolyl tetramethylbutylphenol, phenyldibenzimidazole tetrasulfonate, bis-ethylhexyloxy-phenol-methoxyphenol-triazine, tetrahydroxybenzophenones, terephthalylidene-dicamphor-sulfonic acid, 2,4,6-tris [4,2-ethylhexyloxycarbonyl)anilino]-1,3,5-triazine, methyl-bis(trimethylsiloxy)silyl-isopentyl trimethoxycinnamic acid, amyl-p-dimethylaminobenzoate, amyl-p-dimethylaminobenzoate, 2-ethylhexyl-p-dimethylaminobenzoate, isopropyl-p-methoxycinnamic acid/diisopropylcinnamic acid ester, 2-ethylhexyl-p-methoxycinnamic acid, 2-hydroxy-4-methoxybenzophenone, 2-hydroxy-4-methoxybenzophenone-5-sulfo acid and the trihydrate, and 2-hydroxy-4-methoxybenzophenone-5-sulfonate sodium salt and phenyl-benzimidazole-sulfonic acid.

If the compositions according to the invention contain one or more sunscreen filters, these are contained in the compositions according to the invention preferably in an amount from 0.001 to 30.0 wt %, especially preferably in an amount from 0.05 to 20.0 wt % and quite especially preferably in an amount from 1.0 to 10.0 wt %, relative to the total weight of the corresponding composition according to the invention.

The compositions according to the invention can contain one or more antioxidants, preferably selected from amino acids (e.g. glycine, histidine, tyrosine, tryptophan) and derivatives thereof, imidazoles (e.g. urocaninic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and salts thereof, dilaurylthiodipropionates, distearylthiodipropionates, thiodipropionic acid and derivatives thereof (e.g. esters, ethers, peptides, lipids, nucleotides, nucleosides and salts), and sulfoximine compounds (e.g. buthioninesulfoximines, homocysteine-sulfoximine, buthioninesulfones, penta-, hexa-, heptathioninesulfoximine) in very small compatible dosages, in addition (metal)-chelators (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg-ascorbyl phosphate, ascorbyl acetate), tocopherols and derivatives (e.g. vitamin E-acetate), vitamin A and derivatives (vitamin A-palmitate) and coniferyl benzoate of benzoic resin, rutinic acid and derivatives thereof, α-glycosyl-rutin, ferulic acid, furfurylidene glucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenium methionine), stilbenes and derivatives thereof (e.g. stilbene oxide, trans-stilbene oxide), superoxide dismutase and the derivatives (salts, esters, ethers, sugars, nucleotides, nucleosides, peptides and lipids) of the aforementioned substances that are suitable according to the invention.

The antioxidants can protect the skin and the hair against oxidative stress. Preferred antioxidants are vitamin E and its derivatives and vitamin A and its derivatives.

If the compositions according to the invention contain one or more antioxidants, these are contained in the compositions according to the invention preferably in an amount from 0.001 to 30.0 wt %, especially preferably in an amount from 0.05 to 20.0 wt % and quite especially preferably in an amount from 1.0 to 10.0 wt %, relative to the total weight of the corresponding composition according to the invention.

In addition, humectants can be used, selected from the sodium salt of 2-pyrrolidone-5-carboxylate (NaPCA), guanidine; glycolic acid and salts thereof, lactic acid and salts thereof, glucosamines and salts thereof, lactamide monoethanolamine, acetamide monoethanolamine, urea, hydroxyethylurea, hydroxy acids, panthenol and its derivatives, for example D-panthenol (R-2,4-dihydroxy-N-(3-hydroxypropyl)-3,3-dimethylbutamide), D,L-panthenol, calcium pantothenate, panthetine, pantotheine, panthenyl ethyl ether, isopropyl palmitate, glycerol and/or sorbitol. If the compositions according to the invention contain one or more humectants, these are contained in the compositions according to the invention preferably in an amount from 0.1 to 15.0 wt % and especially preferably in an amount from 0.5 to 5.0 wt %, relative to the total weight of the corresponding composition according to the invention.

In addition, the compositions according to the invention can contain organic solvents. In principle, all mono- or polyhydric alcohols may come into consideration as organic solvents. Alcohols with 1 to 4 carbon atoms such as ethanol, propanol, isopropanol, n-butanol, i-butanol, tert-butanol, glycerol and mixtures of the aforesaid alcohols are preferably used. Other preferred alcohols are polyethylene glycols with a relative molecular weight below 2000. In particular, use of polyethylene glycol with a relative molecular weight between 200 and 600 and in amounts of up to 45.0 wt % and of polyethylene glycol with a relative molecular weight between 400 and 600 in amounts from 5.0 to 25.0 wt % is preferred. Other suitable solvents are for example triacetin (glycerol triacetate) and 1-methoxy-2-propanol.

The compositions according to the invention can contain one or more substances selected from colorants, e.g. dyes and/or pigments. The dyes and/or pigments, both organic and inorganic dyes and pigments, contained in the formulations according to the invention are selected from the relevant positive list of the Cosmetics Directive or the EC list of cosmetic colorants.

| Chemical or other designation | CIN | Color |
|---|---|---|
| Pigment Green | 10006 | Green |
| Acid Green 1 | 10020 | Green |
| 2,4-Dinitrohydroxynaphthalene-7-sulfo acid | 10316 | Yellow |
| Pigment Yellow 1 | 11680 | Yellow |
| Pigment Yellow 3 | 11710 | Yellow |
| Pigment Orange 1 | 11725 | Orange |
| 2,4-Dihydroxyazobenzene | 11920 | Orange |
| Solvent Red 3 | 12010 | Red |
| 1-(2'-Chloro-4'-nitro-1'-phenylazo)-2-hydroxynaphthalene | 12085 | Red |
| Pigment Red 3 | 12120 | Red |
| Ceres Red; Sudan Red; Fat Red G | 12150 | Red |
| Pigment Red 112 | 12370 | Red |
| Pigment Red 7 | 12420 | Red |
| Pigment Brown 1 | 12480 | Brown |
| 4-(2'-Methoxy-5'-sulfo acid diethylamide-1'-phenylazo)-3-hydroxy-5''-chloro-2'',4''-dimethoxy-2-naphthoic acid anilide | 12490 | Red |
| Disperse Yellow 16 | 12700 | Yellow |
| 1-(4-Sulfo-1-phenylazo)-4-amino-brezol-sulfo acid | 13015 | Yellow |
| 2,4-Dihydroxy-azobenzene-4'-sulfo acid | 14270 | Orange |
| 2-(2,4-Dimethylphenylazo-5-sulfo acid)-1-hydroxynaphthalene-4-sulfo acid | 14700 | Red |
| 2-(4-Sulfo-1-naphthylazo)-1-naphthol-4-sulfo acid | 14720 | Red |
| 2-(6-Sulfo-2,4-xylylazo)-1-naphthol-5-sulfo acid | 14815 | Red |
| 1-(4'-Sulfophenylazo)-2-hydroxynaphthalene | 15510 | Orange |
| 1-(2-Sulfo acid-4-chloro-5-carboxylic acid-1-phenylazo)-2-hydroxynaphthalene | 15525 | Red |
| 1-(3-Methyl-phenylazo-4-sulfo acid)-2-hydroxynaphthalene | 15580 | Red |
| 1-(4',(8')-Sulfo acid naphthylazo)-2-hydroxynaphthalene | 15620 | Red |
| 2-Hydroxy-1,2'-azonaphthalene-1'-sulfo acid | 15630 | Red |
| 3-Hydroxy-4-phenylazo-2-naphthylcarboxylic acid | 15800 | Red |
| 1-(2-Sulfo-4-methyl-1-phenylazo)-2-naphthylcarboxylic acid | 15850 | Red |
| 1-(2-Sulfo-4-methyl-5-chloro-1-phenylazo)-2-hydroxynaphthalene-3-carboxylic acid | 15865 | Red |
| 1-(2-Sulfo-1-naphthylazo)-2-hydroxynaphthalene-3-carboxylic acid | 15880 | Red |
| 1-(3-Sulfo-1-phenylazo)-2-naphthol-6-sulfo acid | 15980 | Orange |
| 1-(4-Sulfo-1-phenylazo)-2-naphthol-6-sulfo acid | 15985 | Yellow |
| Allura Red | 16035 | Red |
| 1-(4-Sulfo-1-naphthylazo)-2-naphthol-3,6-disulfo acid | 16185 | Red |
| Acid Orange 10 | 16230 | Orange |
| 1-(4-Sulfo-1-naphthylazo)-2-naphthol-6,8-disulfo acid | 16255 | Red |
| 1-(4-Sulfo-1-naphthylazo)-2-naphthol-3,6,8-trisulfo acid | 16290 | Red |
| 8-Amino-2-phenylazo-1-naphthol-3,6-disulfo acid | 17200 | Red |

-continued

| Chemical or other designation | CIN | Color |
|---|---|---|
| Acid Red 1 | 18050 | Red |
| Acid Red 155 | 18130 | Red |
| Acid Yellow 121 | 18690 | Yellow |
| Acid Red 180 | 18736 | Red |
| Acid Yellow 11 | 18820 | Yellow |
| Acid Yellow 17 | 18965 | Yellow |
| 4-(4-Sulfo-1-phenylazo)-1-(4-sulfophenyl)-5-hydroxy-phrazolone-3-carboxylic acid | 19140 | Yellow |
| Pigment Yellow 16 | 20040 | Yellow |
| 2,6-(4'-Sulfo-2'',4''-dimethyl)-bis-phenylazo)1,3-dihydroxybenzene | 20170 | Orange |
| Acid Black 1 | 20470 | Black |
| Pigment Yellow 13 | 21100 | Yellow |
| Pigment Yellow 83 | 21108 | Yellow |
| Solvent Yellow | 21230 | Yellow |
| Acid Red 163 | 24790 | Red |
| Acid Red 73 | 27290 | Red |
| 2-[4'-(4''Sulfo-1''-phenylazo)-7'-sulfo-1'-naphthylazo]-1-hydroxy-7-aminonaphthalene-3,6-disulfo acid | 27755 | Black |
| 4'-[(4''-Sulfo-1''-phenylazo)-7'-sulfo-1'-naphthylazo]-1-hydroxy-8-acetyl-aminonaphthalene-3,5-disulfo acid | 28440 | Black |
| Direct Orange 34, 39, 44, 46, 60 | 40215 | Orange |
| Food Yellow | 40800 | Orange |
| trans-β-Apo-8'-carotene aldehyde ($C_{30}$) | 40820 | Orange |
| trans-Apo-8'-carotene acid ($C_{30}$) ethyl ester | 40825 | Orange |
| Canthaxanthine | 40850 | Orange |
| Acid Blue 1 | 42045 | Blue |
| 2,4-Disulfo-5-hydroxy-4'-4''-bis-(diethylamino)triphenyl-carbinol | 42051 | Blue |
| 4-[(-4-N-Ethyl-p-sulfobenzylamino)-phenyl-(4-hydroxy-2-sulfophenyl)-(methylene)-1-(N-ethyl-N-p-sulfobenzyl)-2,5-cyclohexadienimine] | 42053 | Green |
| Acid Blue 7 | 42080 | Blue |
| (N-Ethyl-p-sulfobenzyl-amino-phenyl-(2-sulfophenyl)-methylene-(N-ethyl-N-p-sulfobenzyl)-cyclohexadienimine | 42090 | Blue |
| Acid Green 9 | 42100 | Green |
| Diethyl-di-sulfobenzyl-di-4-amino-2-chloro-di-2-methyl-fuchsonimmonium | 42170 | Green |
| Basic Violet 14 | 42510 | Violet |
| Basic Violet 2 | 42520 | Violet |
| 2'-Methyl-4'-(N-ethyl-N-m-sulfobenzyl)-amino-4''-(N-diethyl)-amino-2-methyl-N-ethyl-N-m-sulfobenzyl-fuchsonimmonium | 42735 | Blue |
| 4'-(N-Dimethyl)-amino-4''-(N-phenyl)-aminonaphtho-N-dimethyl-fuchsonimmonium | 44045 | Blue |
| 2-Hydroxy-3,6-disulfo-4,4'-bis-dimethylaminonaphthofuchsinimmonium | 44090 | Green |
| Acid Red | 45100 | Red |
| 3-(2'-Methylphenylamino)-6-(2'-methyl-4'-sulfophenylamino)-9-(2''-carboxyphenyl)-xanthenium salt | 45190 | Violet |
| Acid Red 50 | 45220 | Red |
| Phenyl-2-oxyfluorone-2-carboxylic acid | 45350 | Yellow |
| 4,5-Dibromofluorescein | 45370 | Orange |
| 2,4,5,7-Tetrabromofluorescein | 45380 | Red |
| Solvent Dye | 45396 | Orange |
| Acid Red 98 | 45405 | Red |
| 3',4',5',6'-Tetrachloro-2,4,5,7-tetrabromofluorescein | 45410 | Red |
| 4,5-Diiodofluorescein | 45425 | Red |
| 2,4,5,7-Tetraiodofluorescein | 45430 | Red |
| Quinophthalone | 47000 | Yellow |
| Quinophthalone-disulfo acid | 47005 | Yellow |
| Acid Violet 50 | 50325 | Violet |
| Acid Black 2 | 50420 | Black |
| Pigment Violet 23 | 51319 | Violet |
| 1,2-Dioxyanthraquinone, calcium-aluminum complex | 58000 | Red |
| 3-Oxypyrene-5,8,10-sulfo acid | 59040 | Green |
| 1-Hydroxy-4-N-phenyl-aminoanthraquinone | 60724 | Violet |
| 1-Hydroxy-4-(4'-methylphenylamino)-anthraquinone | 60725 | Violet |
| Acid Violet 23 | 60730 | Violet |
| 1,4-Di(4'-methyl-phenylamino)-anthraquinone | 61565 | Green |
| 1,4-Bis(o-sulfo-p-toluidine)-anthraquinone | 61570 | Green |
| Acid Blue 80 | 61585 | Blue |
| Acid Blue 62 | 62045 | Blue |
| N,N'-Dihydro-1,2,1',2'-anthraquinonazine | 69800 | Blue |

-continued

| Chemical or other designation | CIN | Color |
|---|---|---|
| Vat Blue 6; Pigment Blue 64 | 69825 | Blue |
| Vat Orange 7 | 71105 | Orange |
| Indigo | 73000 | Blue |
| Indigo-disulfo acid | 73015 | Blue |
| 4,4'-Dimethyl-6,6'-dichlorothioindigo | 73360 | Red |
| 5,5'-Dichloro-7,7'-dimethylthioindigo | 73385 | Violet |
| Quinacridone Violet 19 | 73900 | Violet |
| Pigment Red 122 | 73915 | Red |
| Pigment Blue 16 | 74100 | Blue |
| Phthalocyanine | 74160 | Blue |
| Direct Blue 86 | 74180 | Blue |
| Chlorinated phthalocyanine | 74260 | Green |
| Natural Yellow 6, 19; Natural Red 1 | 75100 | Yellow |
| Bixin, Nor-Bixin | 75120 | Orange |
| Lycopene | 75125 | Yellow |
| trans-alpha, beta- or gamma-carotene | 75130 | Orange |
| Keto- and/or hydroxyl derivatives of carotene | 75135 | Yellow |
| Guanine or nacreous agent | 75170 | White |
| 1,7-bis-(4-Hydroxy-3-methoxyphenyl)1,6-heptadiene-3,5-dione | 75300 | Yellow |
| Complex salt (Na,Al,Ca) of carminic acid | 75470 | Red |
| Chlorophyll a and b; copper compounds of chlorophylls and chlorophyllins | 75810 | Green |
| Aluminum | 77000 | White |
| Alumina hydrate | 77002 | White |
| Water-containing aluminum silicates | 77004 | White |
| Ultramarine | 77007 | Blue |
| Pigment Red 101 and 102 | 77015 | Red |
| Barium sulfate | 77120 | White |
| Bismuth oxychloride and mixtures thereof with mica | 77163 | White |
| Calcium carbonate | 77220 | White |
| Calcium sulfate | 77231 | White |
| Carbon | 77266 | Black |
| Pigment Black 9 | 77267 | Black |
| Carbo medicinalis vegetabilis | 77268:1 | Black |
| Chromium oxide | 77288 | Green |
| Chromium oxide, water-containing | 77289 | Green |
| Pigment Blue 28, Pigment Green 14 | 77346 | Green |
| Pigment Metal 2 | 77400 | Brown |
| Gold | 77480 | Brown |
| Iron oxides and hydroxides | 77489 | Orange |
| Iron oxides and hydroxides | 77491 | Red |
| Iron oxide hydrate | 77492 | Yellow |
| Iron oxide | 77499 | Black |
| Mixtures of iron(II) and iron(III) hexacyanoferrate | 77510 | Blue |
| Pigment White 18 | 77713 | White |
| Manganese ammonium diphosphate | 77742 | Violet |
| Manganese phosphate; $Mn_3(PO_4)_2 \cdot 7H_2O$ | 77745 | Red |
| Silver | 77820 | White |
| Titanium dioxide and mixtures thereof with mica | 77891 | White |
| Zinc oxide | 77947 | White |
| 6,7-Dimethyl-9-(1'-D-ribityl)-isoalloxazine, lactoflavin | | Yellow |
| Caramel color | | Brown |
| Capsanthin, capsorubin | | Orange |
| Betanin | | Red |
| Benzopyrillium salts, anthocyanins | | Red |
| Aluminum, zinc, magnesium, and calcium stearate | | White |
| Bromothymol Blue | | Blue |
| Bromocresol Green | | Green |
| Acid Red 195 | | Red |

Oil-soluble natural dyes, e.g. paprika extracts, β-carotene and cochineal, are also advantageous.

The following are also used advantageously: nacreous pigments, e.g. pearl essence (guanine/hypoxanthine mixed crystals from fish scales) and mother of pearl (ground mussel shells), monocrystalline nacreous pigments, e.g. bismuth oxychloride (BiOCl), layer-substrate pigments, e.g. mica/metal oxide, silver-white nacreous pigments from $TiO_2$, interference pigments ($TiO_2$, variable layer thickness), interference pigments ($Fe_2O_3$) and combination pigments ($TiO_2/Fe_2O_3$, $TiO_2/Cr_2O_3$, $TiO_2$/Berlin Blue, $TiO_2$/carmine).

Effect pigments are to be understood in the context of the present invention as pigments that produce special optical effects on account of their refraction properties. Effect pigments endow the treated surface (skin, hair, mucosa) with glossy or glitter effects or can optically conceal skin irregularities and wrinkles through diffuse light scattering. Interference pigments are preferred as a special embodiment of the effect pigments. Particularly suitable effect pigments are for example mica particles, which are coated with at least one metal oxide. In addition to mica, a layered silicate, silica gel and other $SiO_2$-modifications are also suitable as carriers. A metal oxide that is often used for coating is for example titanium oxide, which can if desired be mixed with iron oxide. The reflection properties can be influenced by means of the size and shape (e.g. spherical, ellipsoidal, flattened, even, uneven) of the pigment particles and the thickness of the oxide coating. Other metal oxides, e.g. bismuth oxychloride (BiOCl), and the oxides of for example titanium, especially the $TiO_2$-modifications anatase and rutile, aluminum, tantalum, niobium, zirconium and hafnium also. Effect pigments can also be produced with magnesium fluoride ($MgF_2$) and calcium fluoride (fluorspar, $CaF_2$).

The effects can be controlled both by means of the particle size and by means of the particle size distribution of the pigment population. Suitable particle size distributions are e.g. in the range 2-50 µm, 5-25 µm, 5-40 µm, 5-60 µm, 5-95 µm, 5-100 µm, 10-60 µm, 10-100 µm, 10-125 µm, 20-100 µm, 20-150 µm, and <15 µm. A wider particle size distribution e.g. of 20-150 µm, produces glittering effects, whereas a narrower particle size distribution of <15 µm gives a uniform silky appearance.

If the compositions according to the invention contain one or more effect pigments, these are contained in the compositions according to the invention preferably in an amount from 0.1 to 20.0 wt %, especially preferably in an amount from 0.5 to 10.0 wt % and quite especially preferably in an amount from 1.0 to 5.0 wt %, relative to the total weight of the corresponding composition according to the invention.

Fatty acid monoalkanolamides, fatty acid dialkanolamides, monoesters or diesters of alkylene glycols, especially ethylene glycol and/or propylene glycol or oligomers thereof, with higher fatty acids, e.g. palmitic acid, stearic acid and behenic acid, monoesters or polyesters of glycerol with carboxylic acids, fatty acids and metal salts thereof, ketosulfones or mixtures of the aforementioned compounds are preferred as components producing a nacreous effect.

Ethylene glycol distearates and/or polyethylene glycol distearates with 3 glycol units on average are especially preferred.

If the compositions according to the invention contain one or more pearlescent compounds, these are contained in the compositions according to the invention preferably in an amount from 0.1 to 15.0 wt % and especially preferably in an amount from 1.0 to 10.0 wt %, relative to the total weight of the corresponding composition according to the invention.

Individual fragrance compounds, e.g. the synthetic products of the type of esters, ethers, aldehydes, ketones, alcohols and hydrocarbons can be used as fragrance or perfume oils. Fragrance compounds of the ester type are e.g. benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styralyl propionate and benzyl salicylate. The ethers include for example benzyl ethyl ether, the aldehydes include e.g. the linear alkanals with 8 to 18 carbon atoms, citral, citronellal, citronellyloxyacetaldehyde, cyclamen aldehyde, hydroxycitronellal, filial and bourgeonal, the ketones include e.g. the ionones, alpha-isomethylionone and methyl-cedryl ketone, the alcohols include anethole, citronellol, eugenol, geraniol, linalol, phenylethyl alcohol and terpineol, and the hydrocarbons include mainly the terpenes and balsams. Preferably, mixtures of various fragrances are used, which together produce an attractive perfume note.

Perfume oils can also contain mixtures of natural odoriferous substances that can be obtained from vegetable or animal sources, e.g. pine oil, citrus oil, jasmine oil, lily oil, rose oil, or ylang-ylang oil. Essential oils of lower volatility, which are used mostly as flavor components, are also suitable as perfume oils, e.g. sage oil, chamomile oil, clove oil, melissa oil, mint oil, cinnamon leaf oil, linden flower oil, juniper berry oil, vetiver oil, olibanum oil, galbanum oil and labdanum oil.

Polymer dispersions, especially polyacrylate derivative, polyacrylamide derivative, poly(acrylate derivative-co-acrylamide derivative) dispersions, poly(styrene derivatives-co-acrylate derivative) dispersions, saturated and unsaturated fatty alcohols can be used as opacifiers.

The substances mentioned previously under the silicone oils or waxes can be used as silicones.

Mineral acids, especially HCl, inorganic bases, especially NaOH or KOH, and organic acids, especially citric acid, can preferably be used as acids or alkalis for pH adjustment.

The compositions according to the invention have a pH of preferably 2 to 10, especially preferably from 2 to 7 and quite especially preferably from 2.5 to 6.5.

The polymers according to the invention are advantageously suitable as thickeners, consistency agents, emulsifiers, sensory additives, solubilizers, dispersants, lubricants, adherents, stabilizers or flow point improvers.

Therefore the invention further relates to the use of one or more of the polymers according to the invention as thickener, consistency agent, emulsifier, sensory additive, solubilizer, dispersant, lubricant, adherent, stabilizer or flow point improver, preferably as thickener, consistency agent or sensory additive, especially preferably as thickener or sensory additive and quite especially preferably as sensory additive, very preferably in cosmetic, dermatological or pharmaceutical compositions.

In another preferred embodiment of the invention, the polymers according to the invention are used for stabilizing emulsions, preferably salt-containing emulsions and especially preferably salt-containing cosmetic, dermatological or pharmaceutical emulsions.

The polymers according to the invention are acid-stable and are suitable advantageously for use in cosmetic, dermatological or pharmaceutical compositions with low pH, especially for the care and treatment of body or facial skin.

The present invention therefore further relates to the use of one or more polymers according to the invention for the care and treatment of body or facial skin, preferably in cosmetic, dermatological or pharmaceutical compositions, especially preferably in acidic cosmetic, dermatological or pharmaceutical compositions.

Furthermore, it is advantageous that the polymers according to the invention can be used even without the concomitant use of an additional sensory additive and/or without the concomitant use of an additional thickener in compositions, preferably in cosmetic, dermatological or pharmaceutical compositions. The concomitant use of additional sensory additives and/or thickeners is therefore not essential, but is possible. Combination with other known sensory additives and/or thickeners may be desirable for obtaining special cosmetic profiles and for utilizing synergistic effects. These compositions are preferably in the form of aqueous, aqueous-alcoholic, aqueous surfactant-containing, aqueous-alcoholic surfactant-containing cosmetic, dermatological or pharmaceutical compositions, wherein these preferably do not contain any additional substance selected from sensory additives and additional thickeners.

As already mentioned, in another preferred embodiment of the invention the compositions according to the invention contain one or more substances selected from inorganic and organic UV filters and especially preferably are in the form of a sunscreen composition. In this case the polymers according to the invention have the advantage that they can increase the sunscreen factor of sunscreen compositions.

Therefore the present invention also further relates to the use of one or more of the polymers according to the invention for increasing the sunscreen factor of sunscreen compositions.

The following examples and uses should explain the invention in more detail, but it is not limited to these.

A) EXAMPLES FOR PREPARING POLYMERS ACCORDING TO THE INVENTION

General polymerization specification for preparing the polymers according to the invention by the precipitation method in tert-butanol A 1-liter Quickfit flask with reflux condenser, gas supply, internal thermometer and stirrer is charged with 400 g of tert-butanol, and the calculated amount of 2-acrylamido-2-methyl-propanesulfonic acid (AMPS®, Lubrizol) is added. Then it is neutralized by introducing $NH_3$ (required pH 6-7) and the calculated amount of crosslinking agent is added to the reaction mixture. After inertizing the mixture with $N_2$ or argon, dilauroyl peroxide (DLP) or dimethyl 2,2'-azobis(2-methylpropionate) (V601) is added as initiator at an internal temperature of 60° C., and the polymerization reaction is started. After a few minutes the finished polymer is precipitated. The mixture is heated under reflux for two hours and the polymer is then separated from the solvent on a suction filter and dried in vacuum. This specification is generally applicable for all the polymerization reactions described below.

The general polymerization specification given above was followed for preparing the polymers in the following examples 1-21. In the tables given in the following examples 1-21, the columns on the left give the absolute amounts of the monomers and initiators used for the polymerization (in grams "g") and the columns on the right give the corresponding amounts converted to wt %. The middle columns give the molar proportions of the monomers (in mol %) without taking the initiator into account.

Example 1

| Reactant | g | mol % | wt % |
| --- | --- | --- | --- |
| 2-Acrylamido-2-methyl-propanesulfonic acid | 100.00 | 95.4 | 88.4 |
| Glycerol propoxylate triacrylate (GPTA) | 10.05 | 4.6 | 8.9 |
| Dilauroyl peroxide (DLP) | 3.1 | | 2.7 |

Example 2

| Reactant | g | mol % | wt % |
|---|---|---|---|
| 2-Acrylamido-2-methyl-propanesulfonic acid | 100.00 | 98.9 | 96.4 |
| Glycerol propoxylate triacrylate (GPTA) | 2.37 | 1.1 | 2.3 |
| Dilauroyl peroxide (DLP) | 1.4 | | 1.3 |

Example 3

| Reactant | g | mol % | wt % |
|---|---|---|---|
| 2-Acrylamido-2-methyl-propanesulfonic acid | 100.00 | 99.7 | 98.0 |
| Glycerol propoxylate triacrylate (GPTA) | 0.6 | 0.3 | 0.6 |
| Dilauroyl peroxide (DLP) | 1.4 | | 1.4 |

Example 4

| Reactant | g | mol % | wt % |
|---|---|---|---|
| 2-Acrylamido-2-methyl-propanesulfonic acid | 100.00 | 98.7 | 96.0 |
| Trimethylolpropane propoxytriacrylate (TMPTA-PO-3) | 2.88 | 1.3 | 2.8 |
| Dilauroyl peroxide (DLP) | 1.3 | | 1.2 |

Example 5

| Reactant | g | mol % | wt % |
|---|---|---|---|
| 2-Acrylamido-2-methyl-propanesulfonic acid | 100.00 | 99.4 | 97.4 |
| Trimethylolpropane propoxytriacrylate (TMPTA-PO-3) | 1.38 | 0.6 | 1.3 |
| Dilauroyl peroxide (DLP) | 1.3 | | 1.3 |

Example 6

| Reactant | g | mol % | wt % |
|---|---|---|---|
| 2-Acrylamido-2-methyl-propanesulfonic acid | 100.00 | 98.7 | 96.2 |
| Trimethylolpropane ethoxytriacrylate (TMPTA-EO-3) | 2.62 | 1.3 | 2.5 |
| Dilauroyl peroxide (DLP) | 1.3 | | 1.3 |

Example 7

| Reactant | g | mol % | wt % |
|---|---|---|---|
| 2-Acrylamido-2-methyl-propanesulfonic acid | 100.00 | 97.5 | 92.3 |
| Trimethylolpropane ethoxytriacrylate (TMPTA-EO-3) | 5.3 | 2.5 | 4.9 |
| Dilauroyl peroxide (DLP) | 3.0 | | 2.8 |

Example 8

| Reactant | g | mol % | wt % |
|---|---|---|---|
| 2-Acrylamido-2-methyl-propanesulfonic acid | 100.00 | 98.7 | 93.3 |
| Trimethylolpropane ethoxytriacrylate (TMPTA-EO-15) | 5.85 | 1.3 | 5.5 |
| Dilauroyl peroxide (DLP) | 1.3 | | 1.2 |

Example 9

| Reactant | g | mol % | wt % |
|---|---|---|---|
| 2-Acrylamido-2-methyl-propanesulfonic acid | 100.00 | 97.5 | 88.4 |
| Trimethylolpropane ethoxytriacrylate (TMPTA-EO-15) | 11.81 | 2.5 | 10.4 |
| Dilauroyl peroxide (DLP) | 1.3 | | 1.2 |

Example 10

| Reactant | g | mol % | wt % |
|---|---|---|---|
| 2-Acrylamido-2-methyl-propanesulfonic acid | 100.00 | 95.0 | 79.6 |
| Trimethylolpropane ethoxytriacrylate (TMPTA-EO-15) | 24.25 | 5.0 | 19.3 |
| Dilauroyl peroxide (DLP) | 1.4 | | 1.1 |

Example 11

| Reactant | g | mol % | wt % |
|---|---|---|---|
| 2-Acrylamido-2-methyl-propanesulfonic acid | 100.00 | 99.7 | 97.5 |
| Trimethylolpropane propoxytriacrylate (TMPTA-PO-6) | 0.57 | 0.3 | 0.6 |
| Dilauroyl peroxide (DLP) | 2.0 | | 1.9 |

Example 12

| Reactant | g | mol % | wt % |
|---|---|---|---|
| 2-Acrylamido-2-methyl-propanesulfonic acid | 100.00 | 99.5 | 96.9 |
| Trimethylolpropane propoxytriacrylate (TMPTA-PO-6) | 1.15 | 0.5 | 1.1 |
| Dilauroyl peroxide (DLP) | 2.0 | | 2.0 |

Example 13

| Reactant | g | mol % | wt % |
|---|---|---|---|
| 2-Acrylamido-2-methyl-propanesulfonic acid | 100.00 | 98.7 | 95.3 |
| Trimethylolpropane propoxytriacrylate (TMPTA-PO-6) | 2.88 | 1.3 | 2.7 |
| Dilauroyl peroxide (DLP) | 2.0 | | 2.0 |

Example 14

| Reactant | g | mol % | wt % |
|---|---|---|---|
| 2-Acrylamido-2-methyl-propanesulfonic acid | 100.00 | 97.7 | 93.1 |
| Trimethylolpropane ethoxypropoxytriacrylate (TMPTA-EO-PO) | 5.4 | 2.3 | 5.0 |
| Dilauroyl peroxide (DLP) | 2.0 | | 1.9 |

Example 15

| Reactant | g | mol % | wt % |
|---|---|---|---|
| 2-Acrylamido-2-methyl-propanesulfonic acid | 100.00 | 95.4 | 88.3 |
| Trimethylolpropane ethoxypropoxytriacrylate (TMPTA-EO-PO) | 11.3 | 4.6 | 10.0 |
| Dilauroyl peroxide (DLP) | 2.0 | | 1.7 |

Example 16

| Reactant | g | mol % | wt % |
|---|---|---|---|
| 2-Acrylamido-2-methyl-propanesulfonic acid | 100.00 | 92.8 | 83.3 |
| Trimethylolpropane ethoxypropoxytriacrylate (TMPTA-EO-PO) | 18.0 | 7.2 | 15.0 |
| Dilauroyl peroxide (DLP) | 2.0 | | 1.7 |

Example 17

| Reactant | g | mol % | wt % |
|---|---|---|---|
| 2-Acrylamido-2-methyl-propanesulfonic acid | 100.00 | 99.3 | 96.7 |
| Glycerol propoxylate triacrylate (GPTA) | 1.46 | 0.7 | 1.4 |
| Dilauroyl peroxide (DLP) | 2.0 | | 1.9 |

Example 18

| Reactant | g | mol % | wt % |
|---|---|---|---|
| 2-Acrylamido-2-methyl-propanesulfonic acid | 100.00 | 98.8 | 95.6 |
| Glycerol propoxylate triacrylate (GPTA) | 2.6 | 1.2 | 2.5 |
| Dilauroyl peroxide (DLP) | 2.0 | | 1.9 |

Example 19

| Reactant | g | mol % | wt % |
|---|---|---|---|
| 2-Acrylamido-2-methyl-propanesulfonic acid | 100.00 | 98.8 | 95.5 |
| Trimethylolpropane ethoxytriacrylate (TMPTA-EO-6) | 3.41 | 1.2 | 3.3 |
| Dilauroyl peroxide (DLP) | 1.3 | | 1.2 |

Example 20

| Reactant | g | mol % | wt % |
|---|---|---|---|
| 2-Acrylamido-2-methyl-propanesulfonic acid | 100.00 | 98.7 | 96.1 |
| Trimethylolpropane propoxytriacrylate (TMPTA-PO-3) | 2.88 | 1.3 | 2.8 |
| Dimethyl 2,2'-azobis(2-methylpropionate) (V601) | 1.2 | | 1.1 |

Example 21

| Reactant | g | mol % | wt % |
|---|---|---|---|
| 2-Acrylamido-2-methyl-propanesulfonic acid | 100.00 | 98.8 | 95.6 |
| Trimethylolpropane ethoxytriacrylate (TMPTA-EO-6) | 3.41 | 1.2 | 3.3 |
| Dimethyl 2,2'-azobis(2-methylpropionate) (V601) | 1.2 | | 1.1 |

B) EXAMPLES OF THICKENING IN THE PRESENCE OF SALT AND OF SENSORY TESTING OF THE POLYMERS ACCORDING TO THE INVENTION

B1) Thickening in the Presence of Salt

Polymers according to the invention give rise to a higher viscosity in the presence of salt than the polymer Hostacerin® AMP5 of the company Clariant from the prior art. The viscosities were determined at a polymer concentration of 2 wt % in a solution of 2 wt % sodium chloride in water.

The viscosities were measured with a Brookfield viscosimeter, model DV II, with spindles from the spindle set RV at 20 rev/min and 20° C. Spindles 1 to 7 from spindle set RV are used. In these measurement conditions, spindle 1 is selected for viscosities of max. 500 mPa·s, spindle 2 for viscosities of max. 1000 mPa·s, spindle 3 for viscosities of max. 5000 mPa·s, spindle 4 for viscosities of max. 10 000 mPa·s, spindle 5 for viscosities of max. 20 000 mPa·s, spindle 6 for viscosities of max. 50 000 mPa·s and spindle 7 for viscosities of max. 200 000 mPa·s.

| Polymer | Viscosity (2 wt % polymer in a solution of 2 wt % NaCl in water) [mPa · s] |
|---|---|
| Hostacerin ®AMP5 (comparison) | 4820 |
| Example 18 | 7840 |
| Example 3 | 7880 |
| Example 20 | 9360 |
| Example 7 | 6500 |
| Example 21 | 5040 |
| Example 4 | 9900 |
| Example 6 | 7820 |
| Example 19 | 9500 |

B2) Sensory Testing

In addition, sensory testing was carried out within a panel test with 10 testers, testing the sensory properties of the polymers according to the invention using the following base formulation:

| Ingredient | wt % |
| --- | --- |
| Myritol 318 | 3 |
| Cetiol MM | 2.5 |
| Lanette O | 2 |
| Imwitor 370P | 1 |
| Eutanol G | 1 |
| Polymer | 0.4 |
| Water | to 100 |
| Glycerol | 7.5 |
| Ethanol | 3 |
| Tocopheryl acetate | 1 |
| Aloe barbadensis | 1 |
| NaOH (10 wt % in water) | 0.2 |
| Phenonip | 0.6 |

In this case formulations were prepared using the polymers stated below, using Hostacerin® AMP5 (a polymer corresponding to EP 0 816 403 based on 2-acrylamido-2-methyl-propanesulfonic acid and trimethylolpropane triacrylate as crosslinking agent) as comparative polymer, and were assessed sensorily. The overall assessment of the polymers was assessed with the key ++=very good, +=good, o=satisfactory, −=unsatisfactory.

| Polymer | Sensory properties | Overall assessment |
| --- | --- | --- |
| Hostacerin® AMP5 (comparison) | soaks in slowly, film remains on the skin for a long time, soft skin feel, caring | o |
| Example 18 | soaks in somewhat more quickly than Hostacerin® AMP5, caring for a very long time | ++ |
| Example 3 | good pick-up, soaks in slowly, film remains on the skin for a long time, caring for a long time | + |

C) EXAMPLES OF COSMETIC FORMULATIONS ACCORDING TO THE INVENTION

The following percentages are percentages by weight (wt %), unless explicitly stated otherwise.

The following cosmetic formulations were prepared with polymers according to the invention:

Formulation Examples 1-8

Hand Sanitizer Formulations

| | Formulation No. | | | | | | | |
| --- | --- | --- | --- | --- | --- | --- | --- | --- |
| | 1 | 2 | 3 | 4 | 5 | 6 | 7 | 8 |
| Ingredient | Amount of the respective ingredient [wt %] | | | | | | | |
| Polymer according to example 2 | 1.0 | — | 1.2 | — | 0.8 | — | 1.0 | — |
| Polymer according to example 17 | — | 1.0 | — | 1.2 | — | 1.0 | — | 1.0 |
| Ethanol (96 wt % in water) | 70.0 | 40.0 | — | — | — | 40.0 | 70.0 | 50.0 |
| Isopropanol | — | — | 40.0 | 70.0 | 70.0 | — | — | — |
| Pyroctone Olamine | — | — | — | — | 1.0 | 0.5 | — | 1.0 |
| Triclosan | — | — | — | — | — | — | 0.5 | — |
| Water | 29.0 | 59.0 | 58.8 | 28.8 | 28.2 | 58.5 | 28.5 | 48.0 |

Preparation:
The polymer is stirred into water, the corresponding alcohol, in which antibacterial active substances such as pyroctone olamine or triclosan can be dissolved, is added and it is homogenized. The result is a clear gel.

Formulation Examples 9-12

Hair Care Gels for Strong Hold and Excellent Styling

| | Formulation No. | | | |
| --- | --- | --- | --- | --- |
| | 9 | 10 | 11 | 12 |
| Ingredient | Amount of the respective ingredient [wt %] | | | |
| Polymer according to example 4 | 1.0 | — | 1.0 | — |
| Polymer according to example 17 | — | 1.0 | — | 1.0 |
| Sorbitol | 0.5 | 0.5 | — | — |
| Water | to 100 | to 100 | to 100 | to 100 |
| Carbomer | — | 0.5 | 0.5 | — |
| NaOH | — | q.s. | q.s. | — |
| PEG-40 hydrogenated castor oil | 1.0 | 1.0 | 1.0 | — |
| Fragrance | 0.3 | 0.3 | — | 0.3 |
| Ethanol (96 wt % in water) | 10.0 | 10.0 | 5.0 | — |
| Diaformer Z-712 N (acrylates/lauryl acrylates/stearyl acrylate/ethylamine oxide methacrylate) | 4.5 | 4.5 | — | 6.0 |
| Luviskol VA 64 (PVP/VA) | 3.0 | 3.0 | 5.0 | — |
| Propylene glycol | 1.0 | 1.0 | — | 1.0 |
| Panthenol | 0.5 | 0.5 | — | — |
| Dyestuff solution | q.s. | q.s. | q.s. | — |
| Phenoxyethanol | 1.0 | 1.0 | 0.5 | 0.7 |

Preparation:
The polymers according to example 1 and 2 are dissolved in water (and optionally sorbitol). If carbomer is added, it is then neutralized with NaOH to pH=7. The other components are optionally mixed with PEG-40 hydrogenated castor oil and stirred into the thickened aqueous phase.

Formulation Example 13

Oxidative hair coloring formulation

Coloring basis:

| Ingredient | wt % |
| --- | --- |
| Polyquaternium-29 (dihydroxypropyl chitosan trimonium chloride) | 0.5 |
| m-Phenylenediamine | 0.08 |
| p-Phenylenediamine HCl | 0.30 |
| Resorcinol | 0.25 |

-continued

| Ingredient | wt % |
| --- | --- |
| Sodium bisulfite | 0.30 |
| Sodium laureth sulfate | 3.50 |
| Cetyl alcohol | 15.00 |
| Ammonia (25 wt %, aqueous) | 2.00 |
| Water | to 100 |

Preparation:

Cetyl alcohol and sodium laureth sulfate are heated to 60° C., mixed and introduced with stirring into the aqueous phase, in which the other ingredients have been dissolved.

Developer Gel:

| Ingredient | wt % |
| --- | --- |
| Polymer according to example 6 | 1.5 |
| Hydrogen peroxide (35 wt %, aqueous) | 18 |
| Sodium pyrophosphate | 0.02 |
| 4-Methyl-6-(cyclohexyl)-1-hydroxy-2-pyridone | 0.002 |
| Propylene glycol | 1 |
| Water | to 100 |

Preparation:

4-Methyl-6-(cyclohexyl)-1-hydroxy-2-pyridone is dissolved in propylene glycol. The polymer according to the invention is dissolved in water, then the hydrogen peroxide solution is stirred in, followed by the stabilizer sodium pyrophosphate and the propylene glycol solution.

A gel with a viscosity of approx. 3000 mPa·s at 20° C. is formed.

Coloring Procedure:

50 ml of the color base is stirred with 50 ml of the developer gel and applied to the hair. After 30 minutes it is rinsed out.

Formulation Example 14

Emulsifier-Free Hair Bleaching Gel

| Ingredient | wt % |
| --- | --- |
| Polymer according to example 2 | 1.0 |
| Hydrogen peroxide (35 wt %, aqueous) | 17 |
| Sodium pyrophosphate | 0.02 |
| Sodium stannate | 0.04 |
| 4-Methyl-6-(2,4,4-trimethylpentyl)-1-hydroxy-2-pyridone | 0.001 |
| Propylene glycol | 1 |
| Water | to 100 |

Preparation:

4-Methyl-6-(2,4,4-trimethylpentyl)-1-hydroxy-2-pyridone is dissolved in propylene glycol. The polymer is dissolved in water, then the hydrogen peroxide solution is stirred in, followed by the two stabilizers and the propylene glycol solution.

Formulation Example 15

Fixing Gel for Permanent Waves

| Ingredient | wt % |
| --- | --- |
| Polymer according to example 17 | 0.8 |
| Hydrogen peroxide (35 wt %, aqueous) | 5 |
| Sodium pyrophosphate | 0.02 |
| 4-Methyl-6-(2,4,4-trimethylpentyl)-1-hydroxy-2-pyridone | 0.002 |
| Propylene glycol | 1 |
| Water | to 100 |

Preparation:

4-Methyl-6-(2,4,4-trimethylpentyl)-1-hydroxy-2-pyridone is dissolved in propylene glycol.

The polymer is dissolved in water, the hydrogen peroxide solution and the pyrophosphate plus the propylene glycol solution are introduced and it is homogenized.

Formulation Example 16

O/W Exfoliating Cream with High Electrolyte Content (Na Glycolate)

| Phase | Ingredient | wt % |
| --- | --- | --- |
| A | PEG-120 methyl glucose dioleate | 1.5 |
| B | Water | to 100 |
| C | Mineral oil | 5.0 |
|   | Caprylyl trimethicone | 3.0 |
| D | Polymer according to example 8 | 1.2 |
| E | Glycolic acid 30 wt % in water (neutralized with NaOH to pH = 4) | 6.0 |
|   | Preservative | q.s. |
| F | Laureth-7 | 3.0 |

Preparation:

Dissolve A in phase B while heating. Disperse phase C in phase D and stir into the aqueous phase. Then stir in phases E and F.

Formulation Example 17

W/O Skin Care Milk

| Phase | Ingredient | wt % |
| --- | --- | --- |
| A | Amodimethicone glycerocarbamate | 2.0 |
|   | Cyclopentasiloxane | 5.0 |
|   | Paraffin oil | 3.5 |
|   | Apricot kernel oil | 1.0 |
|   | Grape seed oil | 0.5 |
|   | Microcrystalline wax | 0.7 |
|   | Stearic acid | 0.5 |
|   | Ethylhexyl cocoate | 7.0 |
| B | Polymer according to example 13 | 0.3 |
| C | Water | to 100 |
|   | Glycerol | 3.5 |
|   | Preservative | q.s. |

Preparation:

Heat the oil phase A to 80° C. and stir in polymer B. Add phase C slowly in small portions, stirring vigorously, and leave to cool to room temperature.

Formulation Example 18

Makeup Remover with Excellent Skin Feel

| Phase | Ingredient | wt % |
|---|---|---|
| A | Isopropyl C12-15 Pareth-9 carboxylate | 5.0 |
| B | Sodium cocoyl glutamate (25 wt % solution in water) | 2.3 |
|  | Cocamidopropyl betaine (30 wt % solution in water) | 3.0 |
|  | Laureth-7 | 2.0 |
|  | Water | to 100 |
|  | Allantoin | 0.3 |
|  | Polypropylene terephthalate | 1.0 |
|  | 1,6-Hexanediol | 2.0 |
|  | Propylene glycol | 2.0 |
|  | PEG-8 | 2.0 |
|  | Panthenol | 0.5 |
|  | Poloxamer 407 | 3.0 |
|  | Preservative | q.s. |
|  | Polymer according to example 17 | 1.0 |

Preparation:

Dissolve the components of B one after another in A.

Formulation Example 19

Shampoo/Shower Gel with Suspended Particles

| Phase | Ingredient | wt % |
|---|---|---|
| A | Water | to 100 |
| B | Polymer according to example 2 | 2.0 |
| C | Sodium laureth sulfate (30 wt % in water) | 18.5 |
|  | Perfume | 0.5 |
|  | Preservative | q.s. |
| D | Sodium cocoyl glutamate (25 wt % solution in water) | 20.0 |
| E | Synthetic wax | 0.2 |

Preparation:

Dissolve the polymer in water, then introduce phases C, D and E in succession and homogenize.

Formulation Example 20

Clear Deodorizing Gel

| Phase | Ingredient | wt % |
|---|---|---|
| A | PEG-40 hydrogenated castor oil | 1.0 |
|  | Perfume | 0.1 |
| B | Ethanol (96 wt % in water) | 25.0 |
|  | Pyroctone Olamine (Octopirox ®, Clariant) | 0.1 |
| C | Propylene glycol | 20.0 |
|  | Diisopropyl adipate | 1.0 |
|  | Water | to 100 |
|  | Benzyl alcohol, methylparaben, propylparaben | 0.2 |
| D | Polymer according to example 13 | 1.3 |
| E | Citric acid | q.s. |

Preparation:

Phase A is mixed, then phase B and phase C are added one after another and the pH is adjusted with phase E to pH=5.5. Finally phase D is stirred in, until a homogeneous clear gel has formed.

Formulation Example 21

Matting Serum

| Phase | Ingredient | wt % |
|---|---|---|
| A | Water | to 100 |
| B | Glycerol | 3.0 |
|  | Polymer according to example 5 | 0.5 |
|  | Caprylyl methicone | 1.5 |
|  | Cyclomethicone and dimethicone crosspolymer (Dow Corning 9040 silicone elastomer blend) | 1.0 |
|  | Fragrance | 0.15 |
|  | Preservative | q.s. |

Preparation:

The components of B are stirred into phase A one after another.

Formulation Example 22

Skin Whitening Gel

| Phase | Ingredient | wt % |
|---|---|---|
| A | Allantoin | 0.5 |
| B | Water | to 100 |
| C | Xanthan gum | 0.5 |
| D | Ascorbic acid 2-glucoside | 2.0 |
| E | NaOH (25 wt % solution in water) | q.s. |
| F | Glycerol | 10.0 |
|  | Ethanol (96 wt % in water) | 10.0 |
|  | PEG/PPG-18/18 dimethicone (Dow Corning ® 190, Dow Corning) | 1.0 |
|  | PEG-40 hydrogenated castor oil | 0.8 |
| G | Polymer according to example 17 | 1.0 |
| H | NaOH (25 wt % solution in water) | q.s. |
| I | DMDM hydantoin | q.s |

Preparation:

Phase A is dissolved in phase B with heating, phase C is stirred in, phase D is added, adjusting to pH=6.5 with phase E. Phase F is mixed and then added, then phase G is added and stirred, until a homogeneous gel is achieved. The pH is optionally adjusted to 6.5 with phase H and the preservative I is stirred in.

Formulation Example 23

Elegant O/W Skin Care Body Lotion with Low Stickiness

| Phase | Ingredient | wt % |
|---|---|---|
| A | Caprylic/capric triglyceride | 3.5 |
|  | Myristyl myristate | 2.5 |
|  | Cetearyl alcohol | 2.0 |
|  | Glyceryl stearate citrate | 1.0 |
|  | Octyldodecanol | 1.0 |
| B | Polymer according to example 17 | 0.6 |
| C | Water | to 100 |
|  | Glycerol | 7.5 |
| D | Ethanol (96 wt % in water) | 3.0 |
|  | Dimethicone | 3.0 |
|  | Tocopheryl acetate | 1.0 |

-continued

| Phase | Ingredient | wt % |
|-------|-----------|------|
|       | *Aloe barbadensis* | 1.0 |
|       | Preservative | q.s. |
|       | Fragrance | q.s. |
| E     | NaOH (10 wt % in water) | q.s. |

Preparation:

Phase A is melted at 70° C., phase B is sprinkled in and phase C, heated to 70° C., is stirred in. After cooling to 35° C., phase D is stirred in, finally adjusting to pH=6 with phase E.

Formulation Example 24

Surfactant-Free Anti-Aging O/W Gel Cream with Wrinkle-Reducing Function

| Phase | Ingredient | wt % |
|-------|-----------|------|
| A | Dicaprylyl ether | 5.0 |
|   | Caprylic/capric triglyceride | 5.0 |
|   | Cetearyl alcohol | 2.0 |
|   | Preservative | q.s. |
| B | Ubiquinone | 0.1 |
| C | Polymer according to example 2 | 1.1 |
| D | Sodium hyaluronate (Dekluron) | 0.3 |
|   | Glycerol | 8.0 |
| E | Water | to 100 |
|   | Mica and titanium dioxide and tin oxide (Prestige ® Soft Orange, Eckart) | 0.5 |
| F | Tocopheryl acetate | 0.3 |
| G | NaOH (10 wt % in water) | q.s |

Preparation:

Phase A is melted at 80° C., phase B and phase C are stirred in one after another. Phase D is first dissolved in phase E and then added. Phase F is stirred in at 35° C., adjusting the pH to 6.0 with phase G. A gel cream is formed.

Formulation Example 25

Surfactant-Free Anti-Aging O/W Gel Cream

| Phase | Ingredient | wt % |
|-------|-----------|------|
| A | Dicaprylyl ether | 5.0 |
|   | Caprylic/capric triglyceride | 5.0 |
|   | Cetearyl alcohol | 2.0 |
|   | Preservative | q.s. |
| B | Ubiquinone | 0.1 |
| C | Polymer according to example 13 | 1.1 |

-continued

| Phase | Ingredient | wt % |
|-------|-----------|------|
| D | Xanthan gum | 0.2 |
|   | Glycerol | 8.0 |
| E | Water | to 100 |
|   | Mica and titanium dioxide and tin oxide (Prestige ® Soft Orange, Eckart) | 0.5 |
| F | Tocopheryl acetate | 0.3 |
| G | NaOH (10 wt % in water) | q.s |

Preparation:

Phase A is melted at 80° C., and phase B and phase C are stirred in one after another. Phase D is first dissolved in phase E and then added. Phase F is stirred in at 35° C., adjusting the pH to 6.0 with phase G. A gel cream is formed.

Formulation Example 26

O/W Self-Tanning Cream with Moisturizing Effect

| Phase | Ingredient | wt % |
|-------|-----------|------|
| A | Cetyl phosphate | 1.0 |
|   | Glyceryl stearate | 0.5 |
|   | Cetearyl alcohol | 0.5 |
|   | Isohexadecane | 8.0 |
|   | Isopropyl palmitate | 7.0 |
|   | Caprylyl methicone | 1.0 |
| B | Polymer according to example 17 | 1.0 |
| C | Water | to 100 |
|   | Sodium cocoyl glutamate | 0.5 |
|   | Glycerol | 5.0 |
|   | NaOH (10 wt % in water) | 0.5 |
| D | Tocopheryl acetate | 1.0 |
|   | Fragrance | 0.2 |
|   | Preservative | q.s. |
| E | Dihydroxyacetone | 5.0 |
|   | Water | 8.0 |

Preparation:

Phase A is melted at 80° C., and phase B and phase C are stirred in one after another. Phase D is added at 30° C. and phase E is finally stirred in. The result is a cream with a pH of 4.2.

Formulation Examples 27-32

W/O Sunscreen Formulations with High Protection Factor

In sunscreen products, the polymers according to the invention contribute to better dispersibility of the sunscreen formulation and endow the cosmetic and pharmaceutical product with a pleasant skin feel and good spreading capacity.

The sunscreen formulations shown in the following table were prepared.

| | Formulation No. | | | | | |
|---|---|---|---|---|---|---|
| | 27 | 28 | 29 | 30 | 31 | 32 |
| Ingredient | Amount of the respective ingredient [wt %] | | | | | |
| $C_{12-15}$ alkyl benzoate | 8 | 8 | 8 | 8 | 8 | 8 |
| Caprylic capric triglyceride | 5 | 5 | 5 | 5 | 5 | 5 |
| Octocrylene | 9 | — | 5 | 4 | — | — |
| Ethylhexyl methoxycinnamate | 7 | 7 | 7 | — | 6 | 6 |

-continued

| Ingredient | 27 | 28 | 29 | 30 | 31 | 32 |
|---|---|---|---|---|---|---|
| | Amount of the respective ingredient [wt %] | | | | | |
| Butyl Methoxydibenzoylmethane | 2.5 | — | 2.5 | — | — | — |
| Disodium phenyl dibenzimidazole tetrasulfonate | — | — | — | — | — | 3 |
| Ethylhexyl bis-isopentylbenzoxazolyl-phenyl-melamine | — | — | — | — | 2 | — |
| Diethylamino hydroxybenzoyl hexyl benzoate | — | — | 2 | 1 | — | — |
| Bis Ethylhexyloxyphenol methoxyphenyl triazine | — | 3 | — | 2 | 4 | 3 |
| Methylene Bis-Benzotriazolyl Tetramethylbutyiphenol | — | 3 | — | — | — | 2 |
| Ethylhexyl triazone | — | — | — | 3 | — | — |
| Diethylhexyl butamido triazone | — | — | — | — | 2 | — |
| Polysilicone-15 | — | — | 2 | — | — | — |
| Phenylbenzimidazole sulfonic acid | — | — | — | 3 | — | — |
| Titanium dioxide | — | 5 | 3 | 4 | 5 | 5 |
| Cetearyl alcohol | 1 | 1 | 1 | 1 | 1 | 1 |
| Sunflower seed oil Sorbitol esters | 2 | 2 | 2 | 2 | 2 | 2 |
| Preservative | q.s. | q.s. | q.s. | q.s. | q.s. | q.s. |
| Potassium cetylphosphate | 3 | 3 | 3 | 3 | 3 | 3 |
| Polymer according to example 4 | 1 | 0.6 | — | — | — | — |
| Polymer according to example 8 | — | — | 0.5 | 0.9 | — | — |
| Polymer according to example 17 | — | — | — | — | 1 | 1 |
| Water | to 100 | to 100 | to 100 | to 100 | to 100 | to 100 |
| Nylon | — | 0.5 | — | — | — | — |
| Bis-Ethylhexyl Hydroxydimethoxy Benzylmalonate | — | — | 1 | — | — | — |
| Talc | — | — | — | — | 0.5 | — |

Preparation:

For preparation, the oil-soluble components were heated to 80° C., potassium cetylphosphate and the polymer according to the invention were sprinkled in one after another and the combined water-soluble phases were introduced slowly, stirring vigorously, into the oil phase. The emulsions that formed were left to cool to room temperature, with stirring.

The sunscreen filters used in formulation examples 27-32, their brand names and their UV protection range are presented in the following table.

| Sunscreen filter | Brand name | Protection range (UV-A/UV-B) |
|---|---|---|
| Octocrylene | Neo Heliopan ® 303 | B |
| Ethylhexyl methoxycinnamate | Neo Heliopan ® AV | B |
| Butyl methoxydibenzoylmethane | Neo Heliopan ® 357, Parsol ® 1789 | A |
| Disodium phenyl dibenzimidazole tetrasulfonate | Neo Heliopan ® AP | A |
| Ethylhexyl bis-isopentylbenzoxazolylphenyl-melamine | Uvasorb ® K2A | A |
| Diethylamino hydroxybenzoyl hexyl benzoate | Uvinur ® A Plus | A |
| Bis Ethylhexyloxyphenol methoxyphenyl triazine | Tinosore ® S | A/B |
| Methylene bis-benzotriazolyl tetramethylbutylphenol | Tinosorb ® M | A/B |
| Ethylhexyl triazone | Uvinul ® T150 | B |
| Diethylhexyl butamido triazone | Uvasorb ® HEB | B |
| Polysilicone-15 | Parsol ® SLX | B |
| Phenylbenzimidazole sulfonic acid | | B |

Formulation Example 33

O/W Sunscreen Cream

| Phase | Ingredient | wt % |
|---|---|---|
| A | Ethylhexyl methoxycinnamate | 6.0 |
| | Ethylhexyltriazone | 2.0 |

-continued

| Phase | Ingredient | wt % |
|---|---|---|
|   | Benzophenone-3 | 2.0 |
|   | BHT | 0.05 |
| B | Polymer according to example 2 | 1.5 |
|   | Trilaureth-4 phosphate | 2.0 |
|   | Polyglyceryl-2 sesquiisostearate | 1.0 |
|   | Caprylyl methicone | 1.0 |
|   | Phenonip ®, Clariant | 0.6 |
|   | PVP/hexadecene copolymer | 1.0 |
|   | Tocopheryl acetate | 0.5 |
|   | Fragrance | 0.2 |
| C | Water | to 100 |
|   | Disodium EDTA | 0.1 |
| D | Methylene bis-benzotriazolyl tetramethylbutylphenol | 4.0 |
| E | With triethanolamine to pH 6.8-7.2 | q.s. |

Preparation:

Homogenize phase A and dissolve at 60° C. and stir into phase B, then add phase C with stirring and stir at 300 revolutions per minute. Then phase D is stirred in, adjusting the pH with E.

Formulation Example 34

Sprayable O/W Lotion

| Phase | Ingredient | wt % |
|---|---|---|
| A | Trilaureth-4 phosphate | 1.0 |
|   | Mineral oil | 8.0 |
|   | Isopropyl palmitate | 3.0 |
|   | Cetearyl alcohol | 0.5 |
|   | Caprylic/capric triglyceride | 2.0 |
|   | Glyceryl stearate | 0.5 |
|   | Caprylyl methicone | 1.0 |
| B | Polymer according to example 17 | 0.4 |
| C | Water | to 100 |
|   | Glycerol | 5.0 |
| D | Fragrance | 0.3 |
|   | Ethanol (96 wt % in water) | 5.0 |
| E | Preservative | q.s |

Preparation:

Heat phase A to 60° C., stir in phase B, then add phase C with stirring and stir at 300 revolutions per minute and leave to cool. Stir in phase D at 35° C., add phase E and finally homogenize.

Formulation Example 35

O/W Foundation

| Phase | Ingredient | wt % |
|---|---|---|
| A | Hydrogenated polydecene | 9.0 |
|   | Caprylic/capric triglyceride | 5.0 |
|   | Caprylyl trimethicone | 4.0 |
|   | Caprylyl methicone | 3.0 |
|   | Steareth-2 | 1.6 |
|   | Steareth-20 | 2.4 |
|   | Polymer according to example 13 | 0.4 |
| B | Kaolin | 1.5 |
|   | Talc | 3.0 |
|   | Iron oxide | 7.9 |
| C | Glycerol | 5.0 |
|   | Water | to 100 |

| Phase | Ingredient | wt % |
|---|---|---|
| D | Preservative | q.s. |
|   | Fragrance | q.s. |

Preparation:

Heat phase A to 70° C., heat phase C to 70° C. Stir phase B into phase A, then add phase C and homogenize well. After cooling to below 40° C., add phase D and homogenize for one minute.

The invention claimed is:

1. A water-soluble or water-swellable polymer, wherein the repeating structural units consist of a) 90.0 to 99.99 mol % of at least one repeating structural unit of formula (1)

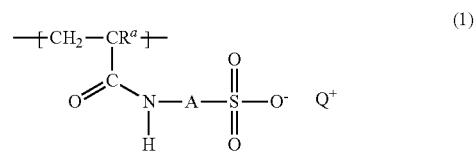

in which $R^a$ is hydrogen, methyl or ethyl,

A is a linear or branched $C_1$-$C_{12}$ alkylene, and $Q^+$ is $H^+$, $NH_4^+$, organic ammonium ions $[HNR^5R^6R^7]^+$, wherein $R^5$, $R^6$ and $R^7$ can be, independently of one another, hydrogen, a linear or branched alkyl group with 1 to 22 carbon atoms, a linear or branched, singly or multiply unsaturated alkenyl group with 2 to 22 carbon atoms, a $C_6$-$C_{22}$ alkylamidopropyl group, a linear monohydroxyalkyl group with 2 to 10 carbon atoms or a linear or branched dihydroxyalkyl group with 3 to 10 carbon atoms, and wherein at least one of the residues $R^5$, $R^6$ and $R^7$ is not hydrogen, alkali$^+$, ½ alkaline-earth$^{++}$, ½ $Zn^{++}$or ⅓ $Al^{+++}$ or mixtures of these ions, and b) 0.01 to 10.0 mol % of at least one repeating crosslinking structural unit of formula (2)

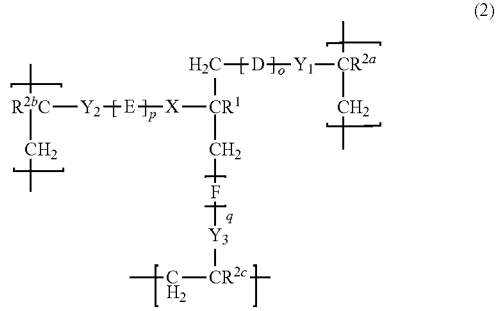

in which $R^1$ is hydrogen, methyl, ethyl, methylol or ethylol, $R_{2a}$, $R^{2b}$ and $R^{2c}$ in each case independently of one another, is hydrogen, methyl or ethyl, X is a chemical bond, methylene, ethylene or a linear or branched alkylene group with 3 carbon atoms, $Y_1$, $Y_2$ and $Y_3$ in each case independently of one another, is a chemical bond, O, $CH_2$, C(O)O, OC(O), C(O)$NR^3$ or $NR^3$C(O), $R^3$ is hydrogen or a linear or branched alkyl residue with 1 to 50 carbon atoms, D, E and F in each case independently of one another, is methylene-oxy, ethylene-oxy, propylene-oxy, a linear or branched alkylene group with 1 to 6 carbon atoms, a linear or branched, singly or multiply unsaturated alkenylene group with 2 to 6 carbon atoms, a linear or branched monohydroxyalkylene group with 2 to 6 carbon atoms or a linear or branched dihydroxyalkylene group with 3 to 6 carbon atoms, and o, p and q in each case independently of one another, is an integer from 0 to 50 and the sum o+p+q≥3.

2. The polymer as claimed in claim 1, wherein the at least one structural unit of formula (1) is derived from 2-acrylamido-2-methyl-propanesulfonic acid or salts thereof.

3. The polymer as claimed in claim 1, wherein the degree of neutralization of the at least one structural unit of formula (1) is from 50.0 to 100 mol %.

4. The polymer as claimed in claim 1, wherein the counterion $Q^+$ that is different from $H^+$ in the at least one structural unit of formula (1) is selected from $NH_4^+$, alkali$^+$, ½ alkaline earth$^{++}$ and mixtures of these ions.

5. The polymer as claimed in claim 1, wherein in the at least one structural unit of formula (2), $R^1$ is hydrogen or ethyl, $R^{2a}$, $R^{2b}$, and $R^{2c}$ in each case independently of one another are hydrogen or methyl, X is a chemical bond or methylene, $Y_1$, $Y_2$ and $Y_3$ in each case independently of one another are C(O)O or OC(O), D, E and F in each case independently of one another are ethylene-oxy or propylene-oxy, o, p and q in each case independently of one another are integers from 0 to 30 and the sum o+p+q is from 3 to 20.

6. The polymer as claimed in claim 1, wherein the at least one structural unit of formula (2) is derived from at least one crosslinking agent selected from the group consisting of glycerol propoxylate triacrylate (GPTA), trimethylolpropane propoxytriacrylate (TMPTA-PO-3) and trimethylolpropane ethoxytriacrylate (TMPTA-EO-3).

7. A cosmetic, dermatological or pharmaceutical composition containing at least one polymer as claimed in claim 1 in an amount from 0.01 to 10.0 wt %, relative to the total weight of the composition.

8. The cosmetic, dermatological or pharmaceutical composition as claimed in claim 7, wherein it is constructed on an aqueous or aqueous-alcoholic basis or is in the form of an emulsion.

9. The cosmetic, dermatological or pharmaceutical composition as claimed in claim 7, further containing at least one substance selected from the group consisting of inorganic and organic salts.

10. The cosmetic, dermatological or pharmaceutical composition as claimed in claim 7, further containing at least one substance selected from the group consisting of alpha- and beta-hydroxy acids.

11. The cosmetic, dermatological or pharmaceutical composition as claimed in claim 7, further containing at least one substance selected from the group consisting of vitamin C and vitamin C derivatives.

12. The cosmetic, dermatological or pharmaceutical composition as claimed in claim 7, further containing at least one substance selected from the group consisting of benzoic acid, sorbic acid, salicylic acid, lactic acid and paramethoxybenzoic acid.

13. The cosmetic, dermatological or pharmaceutical composition as claimed in claim 7, further containing at least one antimicrobial active substance and is in the form of a disinfectant gel.

14. The cosmetic, dermatological or pharmaceutical composition as claimed in claim 7, further containing at least one substance selected from the group consisting of inorganic and organic UV filters and is in the form of a sunscreen composition.

15. The cosmetic, dermatological or pharmaceutical composition as claimed in claim 7, wherein it has a pH from 2 to 10.

16. A thickener, consistency agent, emulsifier, sensory additive, solubilizer, dispersant, lubricant, adherent, stabilizer or flow point improver comprising at least one polymer as claimed in claim 1.

17. A process for stabilizing emulsions and salt-containing emulsions comprising the step of adding at least one polymer as claimed in claim 1 to the emulsion or salt-containing emulsion.

* * * * *